US011286237B2

(12) United States Patent
Iwase et al.

(10) Patent No.: US 11,286,237 B2
(45) Date of Patent: Mar. 29, 2022

(54) METHOD FOR MANUFACTURING METHACRYLIC RESIN COMPOSITION

(71) Applicant: ASAHI KASEI KABUSHIKI KAISHA, Tokyo (JP)

(72) Inventors: Katsuhiro Iwase, Tokyo (JP); Harumi Watanabe, Tokyo (JP); Keigo Sasaki, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 15 days.

(21) Appl. No.: 16/920,753

(22) Filed: Jul. 6, 2020

(65) Prior Publication Data

US 2020/0332108 A1 Oct. 22, 2020

Related U.S. Application Data

(60) Continuation of application No. 16/181,370, filed on Nov. 6, 2018, now abandoned, which is a division of application No. 15/618,335, filed on Jun. 9, 2017, now abandoned.

(30) Foreign Application Priority Data

Aug. 30, 2016 (JP) .............................. JP2016-167984
Nov. 24, 2016 (JP) .............................. JP2016-228161

(51) Int. Cl.
| | |
|---|---|
| *C08L 33/10* | (2006.01) |
| *C08F 220/14* | (2006.01) |
| *C07D 207/448* | (2006.01) |
| *C08F 222/00* | (2006.01) |
| *C08L 35/06* | (2006.01) |
| *C08L 33/24* | (2006.01) |

(52) U.S. Cl.
CPC ........ *C07D 207/448* (2013.01); *C08F 220/14* (2013.01); *C08F 222/00* (2013.01); *C08L 33/10* (2013.01); *C08L 33/24* (2013.01); *C08L 35/06* (2013.01)

(58) Field of Classification Search
CPC ...... C08L 33/10; C08F 220/14; C08F 222/00; C07D 207/448
See application file for complete search history.

(56) References Cited

U.S. PATENT DOCUMENTS

| | | | |
|---|---|---|---|
| 7,507,012 B2 | 3/2009 | Aylward et al. | |
| 2006/0171156 A1 | 8/2006 | Sawayanagi et al. | |
| 2009/0137743 A1 | 5/2009 | Ito et al. | |
| 2009/0227738 A1 | 9/2009 | Tanaka et al. | |
| 2010/0202049 A1 | 8/2010 | Kang et al. | |
| 2013/0072651 A1 | 3/2013 | Yonemura et al. | |
| 2014/0128547 A1* | 5/2014 | Yonemura | C08J 5/18 525/205 |
| 2014/0155534 A1* | 6/2014 | Kumazawa | C08L 51/085 524/445 |
| 2015/0299360 A1* | 10/2015 | Murakami | C08F 226/06 428/220 |
| 2017/0031058 A1 | 2/2017 | Kitayama et al. | |

FOREIGN PATENT DOCUMENTS

| | | |
|---|---|---|
| EP | 2514582 A1 | 10/2012 |
| JP | H0689054 B2 | 11/1994 |
| JP | H08302145 A | 11/1996 |
| JP | H09151218 A | 6/1997 |
| JP | H09324016 A | 12/1997 |
| JP | 2001151814 A | 6/2001 |
| JP | 2001233919 A | 8/2001 |
| JP | 2005162835 A | 6/2005 |
| JP | 2005281589 A | 10/2005 |
| JP | 2007254703 A | 10/2007 |
| JP | 2008081539 A | 4/2008 |
| JP | 2008163187 A | 7/2008 |
| JP | 2008191426 A | 8/2008 |
| JP | 2009035694 A | 2/2009 |
| JP | 2010180305 A | 8/2010 |
| JP | 2010211977 A | 9/2010 |
| JP | 2011224934 A | 11/2011 |
| JP | 2013136774 A | 7/2013 |
| JP | 2014028956 A | 2/2014 |

(Continued)

OTHER PUBLICATIONS

Apr. 25, 2018, Office Action issued by the German Patent and Trade Mark Office in the corresponding German Patent Application No. 102017112730.5.
Apr. 27, 2018, Notification of Reasons for Revocation issued by the Japan Patent Office in the corresponding Japanese Patent No. 6151423 with a partial English translation.
Hiroyuki Tadokoro, Microtacticity of Polymers, Polymers, 1962, pp. 398-408, vol. 11, Issue 6, with a partial English translation.
Mar. 14, 2017, Notification of Reasons for Refusal issued by the Japan Patent Office in the corresponding Japanese Patent Application No. 2016-228161.

(Continued)

*Primary Examiner* — Karuna P Reddy
(74) *Attorney, Agent, or Firm* — Kenja IP Law PC

(57) ABSTRACT

Provided is a method for manufacturing a methacrylic resin composition having excellent surface processability and displaying excellent preservability of formed surface processing. A method for manufacturing a methacrylic resin composition, wherein the methacrylic resin composition comprises two or more types of methacrylic resins that each have a structural unit (X) having the same type of cyclic structure-containing main chain, the methacrylic resin composition has a Vicat softening temperature of 120° C. to 160° C., methanol-soluble content is contained in an amount of 5 mass % or less relative to 100 mass %, in total, of the methanol-soluble content and methanol-insoluble content, comprising mixing a low molecular weight component and a high molecular weight component.

4 Claims, No Drawings

(56) References Cited

FOREIGN PATENT DOCUMENTS

| | | |
|---|---|---|
| JP | 2014069437 A | 4/2014 |
| JP | 2014070187 A | 4/2014 |
| JP | 2014071251 A | 4/2014 |
| JP | 2014080525 A | 5/2014 |
| JP | 2014098117 A | 5/2014 |
| JP | 2015108161 A | 6/2015 |
| JP | 2015135355 A | 7/2015 |
| JP | 2016093959 A | 5/2016 |
| WO | 2011074605 A1 | 6/2011 |
| WO | 2013005634 A1 | 1/2013 |
| WO | 2014061149 A1 | 4/2014 |
| WO | WO-2014061149 A1 * | 4/2014 |
| WO | 2015079694 A1 | 6/2015 |

OTHER PUBLICATIONS

May 23, 2017, Decision to Grant a Patent issued by the Japan Patent Office in the corresponding Japanese Patent Application No. 2016-228161.

* cited by examiner

METHOD FOR MANUFACTURING METHACRYLIC RESIN COMPOSITION

CROSS-REFERENCE TO RELATED APPLICATIONS

The present application is a continuation application of U.S. patent application Ser. No. 16/181,370 filed on Nov. 6, 2018, which is a divisional application of U.S. patent application Ser. No. 15/618,335 filed on Jun. 9, 2017, which claims priority of Japanese Patent Application No. 2016-167984 filed on Aug. 30, 2016, and Japanese Patent Application No 2016-228161 filed on Nov. 24, 2016. The contents of these applications are incorporated herein by reference in their entirety.

TECHNICAL FIELD

This disclosure relates to a method for manufacturing a methacrylic resin composition.

BACKGROUND

Methacrylic resins have excellent transparency, surface hardness, and so forth, and only display a small degree of the optical property of birefringence. For these reasons, methacrylic resins have been attracting attention in recent years as optical resins for various optical materials, and in particular for optical films, and the market for such methacrylic resins is expanding significantly.

In particular, a composition containing a methacrylic resin having a cyclic structure-containing main chain is known to have excellent performance in terms of both heat resistance and optical properties. The demand for such compositions has increased rapidly, focused primarily on applications in relatively thin optical films, such as polarizer protective films and retardation films of image display devices.

Moreover, the market suitably of methacrylic resin-containing compositions is also being investigated with respect to applications in relatively thick molded products, such as light guide plates, display front plates, and so forth for use in displays (for example, liquid-crystal displays and automotive panel displays). These applications exploit the high heat resistance temperature and excellent optical properties of methacrylic resin-containing compositions.

In relation to such molded products for optical components, many studies have been conducted into providing an obtained molded product with new functions by heating the molded product to the glass transition temperature thereof or higher, and then forming fine protrusions and recesses in the surface of the molded product.

In recent years, progress has been made in the investigation of nanometer-scale, fine surface processing techniques by thermal nanoimprinting and the like in applications for relatively thick molded products, such as optical sheets.

For example, in the case of optical film applications, the formation of protrusions and recesses at both sides of a film by a technique referred to as knurling is a known technique for preventing the occurrence of various defects at the surface of the film during long-term storage or transport of the film as a roll-shaped product.

Herein, knurling refers to the formation of fine protrusions and recesses that may also be referred to as embossing. By performing knurling, roll shifting and roll looseness can be prevented, and the occurrence of various defects at the surface of a film can be inhibited by preventing film-on-film adhesion.

The effect of inhibiting the occurrence of various defects through knurling is dependent on the height of knurling protrusions and the contact area between the knurling protrusions and a film surface wound in an overlapping manner on the knurling protrusions.

However, when knurling is performed on a film made of a relatively brittle methacrylic resin, rupturing or cracking of the film itself and deterioration of optical properties imparted by stretching may occur depending on the knurling equipment and processing conditions that are adopted. Accordingly, there is on-going investigation into optimization of knurling equipment and processing conditions.

In relation to methods for enhancing knurling processability of an optical film composed mainly of a methacrylic resin having a cyclic structure-containing main chain, PTL 1, for example, discloses a method of producing an optical film having a knurled section in which the height of protrusions is 25 µm or less and is less than 20% of the height of knurling teeth.

Moreover, PTL 2 proposes a film for which, in the case of a roll-shaped product obtained by winding up an optical film, the area of a knurled section of the film and the area ratio of deformed portions per area of the knurled section are within specific ranges.

The techniques in the patent literature mentioned above relate to the setting of conditions during knurling or the setting of specific conditions in relation to a knurled section of a film, and thus are not necessarily effective if the film conveyance speed during knurling is changed, or if the width or thickness of the produced film is changed. Moreover, since these techniques do not provide improvement from the methacrylic resin having a cyclic structure-containing main chain itself, their scope of applicability may be extremely narrow.

On the other hand, PTL 3 proposes a method for embossing a film formed from a rubber-containing acrylic resin using an embossing die. The proposed method uses an acrylic resin having an elongation at rupture of 100% or more and a storage modulus, which is one type of dynamic viscoelasticity property, that is within a specific range in a temperature range of 25° C. to 50° C. higher than the heat distortion temperature.

However, a resin composition composed mainly of a methacrylic resin having a cyclic structure-containing main chain is known to have a relatively low tensile elongation at break of a few percent to several tens of percent, and also has a high heat distortion temperature. This necessitates a rather high embossing temperature and makes it difficult to adopt the technique in PTL 3 as disclosed.

PTL 4 discloses a stretched film obtained by using an acrylic resin having a cyclic structure-containing main chain and a high toughness amorphous resin (for example, a polycarbonate resin) that is not an acrylic resin having a cyclic structure-containing main chain to produce a film in a manner such that an edge section of the film is formed from the amorphous resin that is not an acrylic resin, and then performing knurling of the edge section formed from the amorphous resin that is not an acrylic resin.

However, this requires highly specialized film production in which two film extruders and a T die having a special structure are used, and in which the resin that is not an acrylic resin is only caused to flow at the edge section of the film. Moreover, a complex process that also includes stretched film formation is required, and thus general-purpose application of this method is likely to be difficult.

CITATION LIST

Patent Literature

PTL 1: JP 2011-224934 A
PTL 2: JP 2014-071251 A
PTL 3: WO 2011/074605 A1
PTL 4: JP 2014-069437 A

SUMMARY

Technical Problem

Irrespective of the current situation described above, with regards to a molded product (for example, an optical film) that is formed from a composition containing a methacrylic resin having a cyclic structure-containing main chain, there is increasing demand for a molded product (for example, an optical film) that includes a knurled section having excellent quality and that is compatible with an increase in production (line) speed associated with progress toward a higher production line speed, thinner film thickness, and commercialization as an elongated roll in order to expand the applications thereof.

Moreover, there are high expectations for the future provision of a methacrylic resin composition having a cyclic structure-containing main chain that has excellent surface shaping properties and can be adopted in a molded product for an optical application or the like that is subjected to surface shaping.

Accordingly, an objective of this disclosure is to provide a method for manufacturing a methacrylic resin composition comprising a methacrylic resin composition with which a molded product having excellent surface shaping properties can be obtained and with which a decrease in quality associated with long-term storage or transport can be inhibited.

Solution to Problem

The inventors conducted diligent investigation to achieve the objective set forth above. As a result, the inventors reached the opinion that, in order to enable stable formation of a protrusion/recess shape at the surface of a molded product, such as a film, by knurling or the like, even in a situation in which the line speed is changed, and in order to enable stable expression of a knurling effect without deformation or damage during transport or long-term storage after subsequent production of a roll-shaped product, it is important that resin properties in a temperature region below the glass transition temperature of a methacrylic resin composition that is used are taken into account in resin design.

As a result of diligent consideration of resin properties in a temperature region below the glass transition temperature, the inventors reached the opinion that, in the case of a methacrylic resin having a raised glass transition temperature due to introduction of a cyclic structure into the main chain thereof, the viscoelastic behavior of the resin in the temperature region below the glass transition temperature is influenced by the stereoregularity of methacrylic acid ester monomer-derived structural units, which are the main constitutional units of the methacrylic resin.

As a result, the inventors discovered that the stereoregularity of methacrylic acid ester monomer-derived structural units in a methacrylic resin having a cyclic structure-containing main chain is influenced not only by the polymerization temperature during radical polymerization in production of the resin, as is conventionally known, but is also strongly influenced by the type and content of a copolymerization monomer, other than a methacrylic acid ester monomer, that is used to introduce the cyclic structure, and other polymerization conditions such as the addition method of copolymerization monomers.

Specifically, the inventors discovered that the problems set forth above can be solved by controlling the stereoregularity of methacrylic acid ester monomer-derived structural units in a methacrylic resin in order to control resin properties in a temperature region below the glass transition temperature of the methacrylic resin, and by additionally controlling the amount of low molecular weight components in the resin composition, which is thought to influence release properties in knurling. The disclosed products were completed based on the discoveries set forth above.

The primary features of this disclosure are as follows.

[1] A method for manufacturing a methacrylic resin composition,
wherein
the methacrylic resin composition comprises two or more types of methacrylic resins that each have a structural unit (X) having the same type of cyclic structure-containing main chain,
the methacrylic resin composition has a Vicat softening temperature of 120° C. to 160° C.,
methanol-soluble content is contained in an amount of 5 mass % or less relative to 100 mass %, in total, of the methanol-soluble content and methanol-insoluble content,
comprising
mixing a low molecular weight component which is a methacrylic resin having a weight average molecular weight (Mw) of 70,000 to 157,000 and a ratio (S/H) of integrated intensity (S) of a syndiotactic fraction (rr) relative to integrated intensity (H) of a heterotactic fraction (mr), as determined by $^1$H-NMR measurement, is 1.10 to 1.40, and a high molecular weight component which is a methacrylic resin having a weight average molecular weight (Mw) of 185,000 to 800,000 and a ratio (S/H) of integrated intensity (S) of a syndiotactic fraction (rr) relative to integrated intensity (H) of a heterotactic fraction (mr), as determined by $^1$H-NMR measurement, is 1.30 to 1.95.

[2] The method for manufacturing a methacrylic resin composition according to the foregoing [1], wherein the methacrylic resin composition has a weight average molecular weight (Mw) of 120,000 to 200,000 as measured by gel permeation chromatography as a polymethyl methacrylate equivalent molecular weight.

[3] The method for manufacturing a methacrylic resin composition according to the foregoing [1], wherein
the structural unit (X) includes an N-substituted maleimide monomer-derived structural unit, and
the N-substituted maleimide monomer-derived structural unit has a content of 5 mass % to 40 mass % relative to 100 mass % of the methacrylic resin.

[4] The method for manufacturing a methacrylic resin composition according to the foregoing [3], wherein
the structural unit (X) includes a lactone ring structural unit, and
the lactone ring structural unit has a content of 5 mass % to 40 mass % relative to 100 mass % of the methacrylic resin.

[5] The method for manufacturing a methacrylic resin composition according to the foregoing [1], wherein the methacrylic resin composition has a photoelastic coefficient with an absolute value of $2.0 \times 10^{-12}$ $Pa^{-1}$ or less.

[6] The method for manufacturing a methacrylic resin composition according to the foregoing [5], wherein the methacrylic resin composition has a photoelastic coefficient with an absolute value of $1.0 \times 10^{-12}$ $Pa^{-1}$ or less.

Advantageous Effect

According to this disclosure, it is possible to provide a methacrylic resin composition with which a molded product having excellent surface shaping properties can be obtained and with which a decrease in quality associated with long-term storage or transport can be inhibited.

DETAILED DESCRIPTION

The following provides a detailed description of an embodiment of the present disclosure (hereinafter, also referred to as the "present embodiment"). However, the present disclosure is not limited by the following description and may be implemented with various modifications within the essential scope thereof.

(Methacrylic Resin Composition)

A methacrylic resin composition according to the present embodiment contains a methacrylic resin, and may contain other thermoplastic resins and additives as necessary.

—Methacrylic Resin—

The methacrylic resin contained in the methacrylic resin composition according to the present embodiment includes a structural unit (X) having a cyclic structure-containing main chain and a methacrylic acid ester monomer-derived structural unit. The structural unit (X) is at least one selected from the group consisting of an N-substituted maleimide monomer-derived structural unit, a glutarimide-based structural unit, and a lactone ring structural unit.

Examples of methods that may be used to produce the methacrylic resin including the structural unit (X) having a cyclic structure-containing main chain include any polymerization method from among bulk polymerization, solution polymerization, suspension polymerization, precipitation polymerization, and emulsion polymerization.

The polymerization process in the production method according to the present embodiment may, for example, be a batch polymerization process, a semi-batch polymerization process, or a continuous polymerization process.

In the production method according to the present embodiment, monomers (detailed description follows below) are preferably polymerized by radical polymerization.

The following description relates, in particular, to each structural unit in the methacrylic resin including the structural unit (X) having a cyclic structure-containing main chain, the methacrylic resin including these structural units, and the production method of this methacrylic resin.

—Methacrylic Acid Ester Monomer-Derived Structural Unit—

First, the methacrylic acid ester monomer-derived structural unit is described.

The methacrylic acid ester monomer-derived structural unit is, for example, formed from a monomer selected from the following methacrylic acid esters. Examples of methacrylic acid esters that can be used include methyl methacrylate, ethyl methacrylate, n-propyl methacrylate, isopropyl methacrylate, n-butyl methacrylate, isobutyl methacrylate, t-butyl methacrylate, 2-ethylhexyl methacrylate, cyclopentyl methacrylate, cyclohexyl methacrylate, cyclooctyl methacrylate, tricyclodecyl methacrylate, dicyclooctyl methacrylate, tricyclododecyl methacrylate, isobornyl methacrylate, phenyl methacrylate, benzyl methacrylate, 1-phenylethyl methacrylate, 2-phenoxyethyl methacrylate, 3-phenylpropyl methacrylate, and 2,4,6-tribromophenyl methacrylate.

One of these monomers may be used individually, or two or more of these monomers may be used together.

Of these methacrylic acid esters, methyl methacrylate and benzyl methacrylate are preferable in terms of providing the resultant methacrylic resin with excellent transparency and weather resistance.

The methacrylic resin may include just one type of methacrylic acid ester monomer-derived structural unit or may include two or more types of methacrylic acid ester monomer-derived structural units.

—Structural Unit (X) Having Cyclic Structure-Containing Main Chain—

The following description relates, in particular, to the structural unit (X) having a cyclic structure-containing main chain in the methacrylic resin that includes the structural unit (X), the methacrylic resin including the structural unit (X), and the production method of this methacrylic resin.

—N-Substituted Maleimide Monomer-Derived Structural Unit—

Next, an N-substituted maleimide monomer-derived structural unit is described.

The N-substituted maleimide monomer-derived structural unit may be formed from at least one selected from a monomer unit represented by the following formula (1) and/or a monomer unit represented by the following formula (2), and is preferably formed from both a monomer represented by the following formula (1) and a monomer represented by the following formula (2).

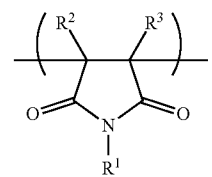

(1)

In formula (1), $R^1$ represents an arylalkyl group having a carbon number of 7 to 14 or an aryl group having a carbon number of 6 to 14, and $R^2$ and $R^3$ each represent, independently of one another, a hydrogen atom, an alkyl group having a carbon number of 1 to 12, or an aryl group having a carbon number of 6 to 14.

Note that in a situation in which $R^2$ is an aryl group, $R^2$ may include a halogen as a substituent.

Moreover, 10 may be substituted with a substituent such as a halogen atom, an alkyl group having carbon number of 1 to 6, an alkoxy group having a carbon number of 1 to 6, a nitro group, or a benzyl group.

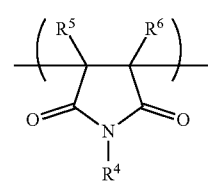

(2)

In formula (2), $R^4$ represents a hydrogen atom, a cycloalkyl group having a carbon number of 3 to 12, or an alkyl group having a carbon number of 1 to 12, and $R^5$ and $R^6$ each represent, independently of one another, a hydrogen atom, an alkyl group having a carbon number of 1 to 12, or an aryl group having a carbon number of 6 to 14.

Specific examples are listed below.

Examples of monomers represented by formula (1) include N-phenylmaleimide, N-benzylmaleimide, N-(2-chlorophenyl)maleimide, N-(4-chlorophenyl)maleimide, N-(4-bromophenyl)maleimide, N-(2-methylphenyl)maleimide, N-(2-ethylphenyl)maleimide, N-(2-methoxyphenyl)maleimide, N-(2-nitrophenyl)maleimide, N-(2,4,6-trimethylphenyl)maleimide, N-(4-benzylphenyl)maleimide, N-(2,4,6-tribromophenyl)maleimide, N-naphthylmaleimide, N-anthracenylmaleimide, 3-methyl-1-phenyl-1H-pyrrole-2,5-dione, 3,4-dimethyl-1-phenyl-1H-pyrrole-2,5-dione, 1,3-diphenyl-1H-pyrrole-2,5-dione, and 1,3,4-triphenyl-1H-pyrrole-2,5-dione.

Of these monomers, N-phenylmaleimide and N-benzylmaleimide are preferable in terms of providing the resultant methacrylic resin with excellent heat resistance and optical properties such as birefringence.

One of these monomers may be used individually, or two or more of these monomers may be used together.

Examples of monomers represented by formula (2) include N-methylmaleimide, N-ethylmaleimide, N-n-propylmaleimide, N-isopropylmaleimide, N-n-butylmaleimide, N-isobutylmaleimide, N-s-butylmaleimide, N-t-butylmaleimide, N-n-pentylmaleimide, N-n-hexylmaleimide, N-n-heptylmaleimide, N-n-octylmaleimide, N-laurylmaleimide, N-cyclopentylmaleimide, N-cyclohexylmaleimide, 1-cyclohexyl-3-methyl-1H-pyrrole-2,5-dione, 1-cyclohexyl-3,4-dimethyl-1H-pyrrole-2,5-dione, 1-cyclohexyl-3-phenyl-1H-pyrrole-2,5-dione, and 1-cyclohexyl-3,4-diphenyl-1H-pyrrole-2,5-dione.

Of these monomers, N-methylmaleimide, N-ethylmaleimide, N-isopropylmaleimide, and N-cyclohexylmaleimide are preferable in terms of providing the resultant methacrylic resin with excellent weather resistance, and N-cyclohexylmaleimide is particularly preferable in terms of providing excellent low water absorbency demanded of optical materials in recent years.

One of these monomers may be used individually, or two or more of these monomers may be used together.

The methacrylic resin according to the present embodiment is particularly preferably obtained using a monomer represented by formula (1) and a monomer represented by formula (2), in combination, in order to exhibit a high level of control on birefringence properties.

The content (B1) of a structural unit derived from the monomer represented by formula (1), in terms of a molar ratio (B1/B2) relative to the content (B2) of a structural unit derived from the monomer represented by formula (2), is preferably greater than 0 and no greater than 15, and more preferably greater than 0 and no greater than 10. When the molar ratio (B1/B2) is within any of the ranges set forth above, the methacrylic resin according to the present embodiment can display good heat resistance and good photoelastic properties while maintaining transparency, and without yellowing or loss of environmental resistance.

The content of the N-substituted maleimide monomer-derived structural unit is not specifically limited so long as the resultant composition has a Vicat softening point (described further below) and an S/H ratio (described below) satisfying ranges according to the present embodiment. However, the content of the N-substituted maleimide monomer-derived structural unit relative to 100 mass % of the methacrylic resin is preferably 5 mass % to 40 mass %, and more preferably 5 mass % to 35 mass %.

When the content of the N-substituted maleimide monomer-derived structural unit is within any of the ranges set forth above, a more adequate enhancement effect can be achieved with respect to heat resistance of the methacrylic resin, and a more preferable enhancement effect can also be achieved with respect to weather resistance, low water absorbency, and optical properties of the methacrylic resin. Restricting the content of the N-substituted maleimide monomer-derived structural unit to 40 mass % or less is effective for preventing a decrease in physical properties of the methacrylic resin caused by a large amount of monomer remaining unreacted due to reduced reactivity of monomer components in the polymerization reaction.

The methacrylic resin according to the present embodiment that includes the N-substituted maleimide monomer-derived structural unit may further include structural units derived from other monomers that are copolymerizable with the methacrylic acid ester monomer and the N-substituted maleimide monomer to the extent that the objectives of the present disclosure are not impeded.

Examples of other copolymerizable monomers that can be used include aromatic vinyls; unsaturated nitriles; acrylic acid esters including a cyclohexyl group, a benzyl group, or an alkyl group having a carbon number of 1 to 18; glycidyl compounds; and unsaturated carboxylic acids. Examples of aromatic vinyls that can be used include styrene, α-methylstyrene, and divinylbenzene. Examples of unsaturated nitriles that can be used include acrylonitrile, methacrylonitrile, and ethacrylonitrile. Examples of acrylic acid esters that can be used include methyl acrylate, ethyl acrylate, propyl acrylate, isopropyl acrylate, and butyl acrylate. Examples of glycidyl compounds that can be used include glycidyl acrylate and allyl glycidyl ether. Examples of unsaturated carboxylic acids that can be used include acrylic acid, methacrylic acid, itaconic acid, maleic acid, and fumaric acid, and half-esterified products and anhydrides thereof.

The methacrylic resin may include just one type of structural unit derived from another copolymerizable monomer, or may include two or more types of structural units derived from other copolymerizable monomers.

The content of structural units derived from such other copolymerizable monomers relative to 100 mass % of the methacrylic resin is preferably 0 mass % to 10 mass %, more preferably 0 mass % to 9 mass %, and even more preferably 0 mass % to 8 mass %.

It is preferable for the content of structural units derived from other monomers to be within any of the ranges set forth above in terms that molding properties and mechanical properties of the resin can be enhanced without losing the intended effects of introducing a cyclic structure into the main chain.

The method used to produce the methacrylic resin including the N-substituted maleimide monomer-derived structural unit in the main chain thereof may be any polymerization method from among bulk polymerization, solution polymerization, suspension polymerization, precipitation polymerization, and emulsion polymerization, is preferably suspension polymerization, bulk polymerization, or solution polymerization, and is more preferably solution polymerization.

The polymerization process in the production method according to the present embodiment may, for example, be a batch polymerization process, a semi-batch polymerization process, or a continuous polymerization process.

In the production method according to the present embodiment, the monomers are preferably polymerized by radical polymerization.

The following provides a specific description of production by radical polymerization using solution polymerization as one example of a method of producing the methacrylic resin including the N-substituted maleimide monomer-derived structural unit (hereinafter, also referred to as a "maleimide copolymer").

A so-called "semi-batch polymerization method" in which a portion of the monomers is charged into a reactor prior to the start of polymerization, a polymerization initiator is added to initiate polymerization, and then a remaining portion of the monomers is subsequently fed into the reactor can be preferably adopted in the present embodiment. Adoption of this method tends to facilitate control of the molecular weight distribution and chemical composition distribution of the resultant polymer.

In production of the maleimide copolymer, a ratio of the amount of the monomers used in initial charging (start of polymerization) and the amount of the monomers added after the start of polymerization (amount of monomers at start of polymerization:amount of monomers added after start of polymerization), in terms of mass ratio, is preferably 1:9 to 8:2, more preferably 2:8 to 7.5:2.5, and even more preferably 3:7 to 5:5.

When the ratio of the amounts of the monomers is within any of the ranges set forth above, the mixing composition of monomers in the initial charge can be selected as appropriate in consideration of copolymerization reactivity of each of the monomers used in copolymerization, which tends to facilitate control of the chemical composition distribution of the resultant polymer.

No specific limitations are placed on the polymerization solvent that is used so long as the solubility of the maleimide copolymer obtained through polymerization is high and an appropriate reaction liquid viscosity can be maintained in order to prevent gelation or the like.

Specific examples of polymerization solvents that can be used include aromatic hydrocarbons such as toluene, xylene, ethylbenzene, and isopropylbenzene; ketones such as methyl isobutyl ketone, butyl cellosolve, methyl ethyl ketone, and cyclohexanone; and polar solvents such as dimethylformamide and 2-methylpyrrolidone.

Moreover, an alcohol such as methanol, ethanol, or isopropanol may be used in combination as the polymerization solvent to the extent that dissolution of the polymerized product during polymerization is not impaired.

No specific limitations are placed on the amount of solvent used in polymerization so long as polymerization proceeds, precipitation of the copolymer or used monomers does not occur in production, and the solvent can be easily removed. For example, when the total amount of used monomers is taken to be 100 parts by mass, the amount of solvent is preferably 10 parts by mass to 200 parts by mass. The amount of solvent is more preferably 25 parts by mass to 200 parts by mass, further preferably 50 parts by mass to 200 parts by mass, and even more preferably 50 parts by mass to 150 parts by mass.

Although no specific limitations are placed on the polymerization temperature other than being a temperature at which polymerization proceeds, the polymerization temperature is preferably 50° C. to 200° C., and more preferably 60° C. to 180° C. from a viewpoint of productivity. Moreover, from a viewpoint of stereoregularity of methyl methacrylate monomer-derived structural units, the polymerization temperature is preferably 70° C. to 130° C., and more preferably 80° C. to 120° C.

Although no specific limitations are placed on the polymerization time other than being a time that enables the required degree of polymerization to be obtained with the required conversion rate, the polymerization time is preferably 0.5 hours to 10 hours, and more preferably 1 hour to 8 hours from a viewpoint of productivity and so forth.

In the polymerization reaction, polymerization may be performed with addition of a polymerization initiator and/or a chain transfer agent as necessary.

The polymerization initiator may be any initiator commonly used in radical polymerization and examples thereof include organic peroxides such as cumene hydroperoxide, diisopropylbenzene hydroperoxide, di-t-butyl peroxide, lauroyl peroxide, benzoyl peroxide, t-butylperoxy isopropyl carbonate, t-amyl peroxy-2-ethylhexanoate, t-amyl peroxyisononanoate, and 1,1-di(t-butylperoxy)cyclohexane; and azo compounds such as 2,2'-azobis(isobutyronitrile), 1,1'-azobis(cyclohexanecarbonitrile), 2,2'-azobis(2,4-dimethylvaleronitrile), and dimethyl-2,2'-azobisisobutyrate.

One of these polymerization initiators may be used individually, or two or more of these polymerization initiators may be used together.

The additive amount of the polymerization initiator when the total amount of monomers used in polymerization is taken to be 100 parts by mass may be 0.01 parts by mass to 1 part by mass, and is preferably 0.05 parts by mass to 0.5 parts by mass.

These polymerization initiators may be added at any stage so long as the polymerization reaction is in progress.

In the present embodiment, it is preferable that the type of initiator, amount of initiator, polymerization temperature, and so forth are appropriately selected such that the total amount of radicals generated by the polymerization initiator as a proportion relative to the total amount of unreacted monomer remaining in the reaction system is constantly no greater than a certain value.

It is particularly preferable in the present embodiment that in the first half of a period from the start of addition of the polymerization initiator to the end of addition of the polymerization initiator (polymerization initiator addition period), there is at least one instance in which the additive amount of the polymerization initiator per unit time is less than the additive amount of the polymerization initiator per unit time at the start of addition.

Adoption of this method can suppress the amount of oligomer or low molecular weight product produced in a latter stage of polymerization and enables improvement of polymerization stability by inhibiting overheating during polymerization.

The chain transfer agent may be a chain transfer agent that is commonly used in radical polymerization and examples thereof include mercaptan compounds such as n-butyl mercaptan, n-octyl mercaptan, n-decyl mercaptan, n-dodecyl mercaptan, and 2-ethylhexyl thioglycolate; halogen compounds such as carbon tetrachloride, methylene chloride, and bromoform; and unsaturated hydrocarbon compounds such as α-methylstyrene dimer, α-terpinene, dipentene, and terpinolene.

One of these chain transfer agents may be used individually, or two or more of these chain transfer agents may be used together.

These chain transfer agents may be added at any stage, without any specific limitations, so long as the polymerization reaction is in progress.

The additive amount of the chain transfer agent when the total amount of monomers used in polymerization is taken to be 100 parts by mass may be 0.01 parts by mass to 1 part by mass, and is preferably 0.05 parts by mass to 0.5 parts by mass.

In solution polymerization, it is important to reduce the concentration of dissolved oxygen in the polymerization solution as much as possible in advance. For example, the concentration of dissolved oxygen is preferably 10 ppm or less. The concentration of dissolved oxygen can be measured, for example, using a dissolved oxygen (DO) meter B-505 (produced by Iijima Electronics Corporation). The method by which the concentration of dissolved oxygen is reduced may be selected as appropriate from methods such as a method in which an inert gas is bubbled into the polymerization solution; a method in which an operation of pressurizing the inside of a vessel containing the polymerization solution to approximately 0.2 MPa with an inert gas and then releasing the pressure is repeated prior to polymerization; and a method in which an inert gas is passed through a vessel containing the polymerization solution.

No specific limitations are placed on the method by which a polymerized product is collected from the polymerization solution obtained through solution polymerization. Examples of methods that can be adopted include a method in which the polymerization solution is added into an excess of a poor solvent in which the polymerized product obtained through polymerization does not dissolve, such as a hydrocarbon solvent or an alcohol solvent, treatment (emulsifying dispersion) is subsequently performed using a homogenizer, and unreacted monomers are separated from the polymerization solution by pre-treatment such as liquid-liquid extraction or solid-liquid extraction; and a method in which the polymerization solvent and unreacted monomers are separated by a step referred to as a devolatilization step to collect the polymerized product.

The devolatilization step is a step in which volatile content such as the polymerization solvent, residual monomers, and reaction by-products are removed under heated vacuum conditions.

Examples of devices that can be used in the devolatilization step include devolatilization devices comprising a tubular heat exchanger and a devolatilization tank; thin film evaporators such as WIPRENE and EXEVA produced by Kobelco Eco-Solutions Co., Ltd., and Kontro and Diagonal-Blade Kontro produced by Hitachi, Ltd.; and vented extruders having sufficient residence time and surface area for displaying devolatilization capability.

Moreover, it is possible to adopt a devolatilization step or the like in which a devolatilization device that is a combination of two or more of these devices is used.

The treatment temperature in the devolatilization device is preferably 150° C. to 350° C., more preferably 170° C. to 300° C., and even more preferably 200° C. to 280° C. A temperature of 150° C. or higher is effective for preventing an excessive amount of residual volatile content. Conversely, a temperature of 350° C. or lower reduces the risk of coloring or decomposition of the resultant methacrylic resin.

The degree of vacuum in the devolatilization device may be 10 Torr to 500 Torr and, within this range, is preferably 10 Torr to 300 Torr. When the degree of vacuum is 500 Torr or less, volatile content has a lower tendency to remain, and when the degree of vacuum is 10 Torr or more, industrial implementation is easier.

The treatment time is selected as appropriate depending on the amount of residual volatile content and is preferably as short as possible in order to inhibit coloring or decomposition of the resultant methacrylic resin.

The polymerized product collected through the devolatilization step is pelletized through a step referred to as a pelletization step.

In the pelletization step, molten resin is extruded from a porous die as strands and is then pelletized by cold cutting, hot cutting in air, strand cutting in water, or under water cutting.

In a situation in which a vented extruder is used as a devolatilization device, the devolatilization step and the pelletization step may be combined.

In one preferable example that may be adopted in the present embodiment, a composition is produced after mixing two or more types of methacrylic resins that include at least a structure derived from a monomer represented by formula (1) and a structure derived from a monomer represented by formula (2) as a framework, but differ in terms of weight average molecular weight and stereoregularity.

Herein, the stereoregularity of a methacrylic resin is expressed by a ratio (S/H) of the integrated intensity (S) of a syndiotactic fraction (rr) relative to the integrated intensity (H) of a heterotactic fraction (mr) among methacrylic acid ester monomer-derived structural units of the methacrylic resin, as determined by $^1$H-NMR measurement.

In the present embodiment, in a situation in which two or more types of methacrylic resins are mixed in production, the weight average molecular weight (Mw) of each of the methacrylic resins, as measured using a differential refractive index detector, may be freely selected from a range of 70,000 to 800,000.

In the case of a methacrylic resin having a low weight average molecular weight (Mw) (hereinafter, also referred to as a "low molecular weight component"), the weight average molecular weight thereof is preferably 70,000 to 150,000, and more preferably 100,000 to 150,000. Moreover, the S/H ratio thereof used as an indicator of stereoregularity is preferably 1.10 to 1.40, and more preferably 1.15 to 1.35.

In the case of a methacrylic resin having a high weight average molecular weight (Mw) (hereinafter, also referred to as a "high molecular weight component"), the weight average molecular weight thereof is preferably 220,000 to 800,000, and more preferably 220,000 to 600,000. Moreover, the S/H ratio thereof used as an indicator of stereoregularity is preferably 1.30 to 1.50, and more preferably 1.35 to 1.50.

In the present embodiment, the mixing ratio of the low molecular weight component and the high molecular weight component is not specifically limited and can be appropriately selected from a range of 5 parts by mass to 95 parts by mass of the low molecular weight component and 95 parts by mass to 5 parts by mass of the high molecular weight component.

Through mixing of two or more types of methacrylic resins as described above, it is possible to provide a resin composition that is suitable for optical films and other molded products that are subjected to surface shaping treatment by knurling or the like.

No specific limitations are placed on the method by which two or more types of methacrylic resins having different weight average molecular weights (Mw) are mixed in the present embodiment. Examples of methods that can be adopted include a method in which liquid-phase mixing of a solution containing two or more types of polymerized products that are obtained through the polymerization reaction described above and have different weight average molecular weights is performed, and then treatment by a devolatilization step or precipitation treatment through addition of a poor solvent is performed; and a method in which mixing is performed using a melt-kneader such as an extruder. Particularly in a situation in which a methacrylic resin having a high molecular weight is used, it is preferable to adopt the method in which liquid-phase mixing of a solution containing two or more types of polymerized products obtained through polymerization reaction is performed, and then treatment by a devolatilization step or precipitation treatment through addition of a poor solvent is performed.

—Glutarimide-Based Structural Unit—

A glutarimide-based structural unit according to the present embodiment is represented by the following general formula (3).

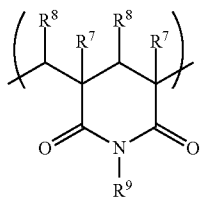

(3)

In general formula (3), it is preferable that $R^7$ and $R^8$ are each, independently of one another, hydrogen or a methyl group, and $R^9$ is hydrogen, a methyl group, a butyl group, or a cyclohexyl group, and more preferable that $R^7$ is a methyl group, $R^8$ is hydrogen, and $R^9$ is a methyl group.

The methacrylic resin may include a single type of glutarimide-based structural unit or may include two or more types of glutarimide-based structural units.

In the methacrylic resin that includes the glutarimide-based structural unit, the content of the glutarimide-based structural unit is not specifically limited so long as the preferable ranges for the Vicat softening point (described below) and S/H ratio (described below) of a composition according to the present embodiment are satisfied. However, the content of the glutarimide-based structural unit relative to 100 mass % of the methacrylic resin is preferably 5 mass % to 70 mass %, and more preferably 5 mass % to 60 mass %.

It is preferable for the content of the glutarimide-based structural unit to be within any of the ranges set forth above in terms that a resin having good molding properties, heat resistance, and optical properties can be obtained.

The methacrylic resin including the glutarimide-based structural unit may further include an aromatic vinyl monomer unit as necessary.

Examples of aromatic vinyl monomers that can be used include, but are not specifically limited to, styrene and α-methylstyrene. The aromatic vinyl monomer is preferably styrene.

The content of the aromatic vinyl unit in the methacrylic resin including the glutarimide-based structural unit is not specifically limited. However, the content of the aromatic vinyl unit relative to 100 mass % of the methacrylic resin is preferably 0 mass % to 10 mass %, more preferably 0 mass % to 9 mass %, and even more preferably 0 mass % to 8 mass %.

It is preferable for the content of the aromatic vinyl unit to be in any of the ranges set forth above in terms that both heat resistance and excellent photoelastic properties can be obtained.

The methacrylic resin including the glutarimide-based structural unit in the main chain thereof may, for example, be a methacrylic resin including a glutarimide-based structural unit described in JP 2006-249202 A, JP 2007-009182 A, JP 2007-009191 A, JP 2011-186482 A, or WO 2012/114718 A1, and may be formed by a method described in the same publication.

—Lactone Ring Structural Unit—

A lactone ring structural unit according to the present embodiment is preferably a six-membered ring since this provides excellent cyclic structure stability.

The lactone ring structural unit that is a six-membered ring is, for example, particularly preferably a structure represented by the following general formula (4).

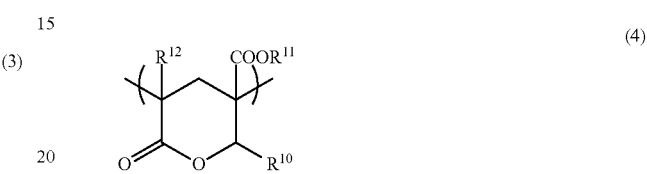

(4)

In general formula (4), $R^{10}$, $R^{11}$, and $R^{12}$ are each, independently of one another, a hydrogen atom or an organic residue having a carbon number of 1 to 20.

Examples of the organic residue include saturated aliphatic hydrocarbon groups (alkyl groups, etc.) having a carbon number of 1 to 20 such as a methyl group, an ethyl group, and a propyl group; unsaturated aliphatic hydrocarbon groups (alkenyl groups, etc.) having a carbon number of 2 to 20 such as an ethenyl group and a propenyl group; aromatic hydrocarbon groups (aryl groups, etc.) having a carbon number of 6 to 20 such as a phenyl group and a naphthyl group; and groups in which at least one hydrogen atom of any of these saturated aliphatic hydrocarbon groups, unsaturated aliphatic hydrocarbon groups, and aromatic hydrocarbon groups is substituted with at least one group selected from the group consisting of a hydroxy group, a carboxyl group, an ether group, and an ester group.

The lactone ring structure may be formed, for example, by copolymerizing an acrylic acid-based monomer having a hydroxy group and a methacrylic acid ester monomer such as methyl methacrylate to introduce a hydroxy group and an ester group or carboxyl group into the molecular chain, and then causing dealcoholization (esterification) or dehydration condensation (hereinafter, also referred to as a "cyclocondensation reaction") between the hydroxy group and the ester group or carboxyl group.

Examples of acrylic acid-based monomers having a hydroxy group that can be used in polymerization include 2-(hydroxymethyl)acrylic acid, 2-(hydroxyethyl)acrylic acid, alkyl 2-(hydroxymethyl)acrylates (for example, methyl 2-(hydroxymethyl)acrylate, ethyl 2-(hydroxymethyl)acrylate, isopropyl 2-(hydroxymethyl)acrylate, n-butyl 2-(hydroxymethyl)acrylate, and t-butyl 2-(hydroxymethyl)acrylate) and alkyl 2-(hydroxyethyl)acrylates. Moreover, 2-(hydroxymethyl)acrylic acid and alkyl 2-(hydroxymethyl) acrylates that are monomers having a hydroxyallyl moiety are preferable, and methyl 2-(hydroxymethyl)acrylate and ethyl 2-(hydroxymethyl)acrylate are particularly preferable.

No specific limitations are placed on the content of the lactone ring structural unit in the methacrylic resin including the lactone ring structural unit in the main chain thereof so long as the ranges for the Vicat softening point (described below) and the S/H ratio (described below) that are preferable for a composition according to the present embodiment are satisfied. However, the content of the lactone ring structural unit relative to 100 mass % of the methacrylic resin is preferably 5 mass % to 40 mass %, and more preferably 5 mass % to 35 mass %.

When the content of the lactone ring structural unit is within any of the ranges set forth above, effects resulting from introduction of a cyclic structure, such as improved solvent resistance and improved surface hardness, can be expressed while maintaining molding properties.

The content of the lactone ring structure in the methacrylic resin can be determined by a method described in the previously mentioned patent literature.

The methacrylic resin including the lactone ring structural unit may include constitutional units derived from other monomers that are copolymerizable with the above-described methacrylic acid ester monomer and acrylic acid-based monomer having a hydroxy group.

Examples of such other copolymerizable monomers include monomers having a polymerizable double bond such as styrene, vinyltoluene, α-methyl styrene, α-hydroxymethylstyrene, α-hydroxy ethyl styrene, acrylonitrile, methacrylonitrile, methallyl alcohol, allyl alcohol, ethylene, propylene, 4-methyl-1-pentene, vinyl acetate, 2-hydroxymethyl-1-butene, methyl vinyl ketone, N-vinylpyrrolidone, and N-vinylcarbazole.

One of these other monomers (constitutional units) may be included, or two or more of these other monomers may be included.

The content of structural units derived from such other copolymerizable monomers relative to 100 mass % of the methacrylic resin is preferably 0 mass % to 10 mass %, more preferably 0 mass % to 9 mass %, and even more preferably 0 mass % to 8 mass %.

The methacrylic resin according to the present embodiment may include one type of structural unit or two or more types of structural units derived from the other copolymerizable monomers described above.

The methacrylic resin including the lactone ring structural unit in the main chain thereof can be formed, for example, by a method described in JP 2001-151814 A, JP 2004-168882 A, JP 2005-146084 A, JP 2006-96960 A, JP 2006-171464 A, JP 2007-63541 A, JP 2007-297620 A, or JP 2010-180305 A.

The method used to produce the methacrylic resin including the lactone ring structural unit is a method in which a lactone ring structure is formed by a cyclization reaction after polymerization. In order to promote this cyclization reaction, it is preferable that monomers are polymerized by radical polymerization through a solution polymerization method that uses a solvent.

In the production method according to the present embodiment, the polymerization process may, for example, be a batch polymerization process, a semi-batch polymerization process, or a continuous polymerization process.

The following provides a specific description of production by radical polymerization through a solution polymerization method as one example of the production method.

A so-called "semi-batch polymerization method" in which a portion of the monomers is charged into a reactor prior to the start of polymerization, a polymerization initiator is added to initiate polymerization, and a remaining portion of the monomers is subsequently fed into the reactor can be preferably adopted in the present embodiment. Adoption of this method tends to facilitate control of the molecular weight distribution and chemical composition distribution of the resultant polymer.

In production of the methacrylic resin including the lactone ring structural unit, a ratio of the amount of the monomers used in initial charging (start of polymerization) and the amount of the monomers added after the start of polymerization (amount of monomers at start of polymerization:amount of monomers added after start of polymerization), in terms of mass ratio, is preferably 1:9 to 8:2, more preferably 2:8 to 7.5:2.5, and even more preferably 3:7 to 5:5.

When the ratio of the amounts of the monomers is within any of the ranges set forth above, the mixing composition of monomers in the initial charge can be selected as appropriate in consideration of copolymerization reactivity of each of the monomers used in copolymerization, which tends to facilitate control of the chemical composition distribution of the resultant polymer.

Examples of the solvent used in polymerization include aromatic hydrocarbons such as toluene, xylene, and ethylbenzene; and ketones such as methyl ethyl ketone and methyl isobutyl ketone.

One of these solvents may be used individually, or two or more of these solvents may be used together.

No specific limitations are placed on the amount of solvent used in polymerization so long as polymerization can proceed and gelation is inhibited. However, when the total amount of monomer that is used is taken to be 100 parts by mass, the amount of solvent is, for example, preferably 50 parts by mass to 200 parts by mass, and more preferably 100 parts by mass to 200 parts by mass.

In order to sufficiently inhibit gelation of the polymerization solution and promote the cyclization reaction after polymerization, polymerization is preferably performed such that the concentration of produced polymer in the reaction mixture obtained after polymerization is 50 mass % or less, and this concentration is preferably controlled to 50 mass % or less by adding polymerization solvent to the reaction mixture as appropriate.

The method by which the polymerization solvent is added to the reaction mixture as appropriate is not specifically limited and may, for example, be through continuous addition of the polymerization solvent or intermittent addition of the polymerization solvent.

The polymerization solvent that is added may be a single type of solvent, or may be a mixed solvent of two or more types of solvents.

Although no specific limitations are placed on the polymerization temperature other than being a temperature at which polymerization proceeds, the polymerization temperature is preferably 50° C. to 200° C., and more preferably 60° C. to 180° C. from a viewpoint of productivity. Moreover, from a viewpoint of stereoregularity of methyl methacrylate monomer-derived structural units, the polymerization temperature is preferably 70° C. to 130° C., and more preferably 80° C. to 120° C.

Although no specific limitations are placed on the polymerization time so long as the target conversion rate can be achieved, the polymerization time is preferably 0.5 hours to 10 hours, and more preferably 1 hour to 8 hours from a viewpoint of productivity and so forth.

In the polymerization reaction, polymerization may be performed with addition of a polymerization initiator and/or a chain transfer agent as necessary.

The polymerization initiator may be, but is not specifically limited to, any of the polymerization initiators disclosed in relation to the production method of the methacrylic resin including the N-substituted maleimide monomer-derived structural unit.

One of these polymerization initiators may be used individually, or two or more of these polymerization initiators may be used together.

The amount of polymerization initiator that is used can be set as appropriate depending on the combination of monomers, reaction conditions, and so forth, without any specific limitations. However, when the total amount of monomer used in polymerization is taken to be 100 parts by mass, the amount of polymerization initiator may be 0.05 parts by mass to 1 part by mass.

These polymerization initiators may be added at any stage so long as the polymerization reaction is in progress.

In the present embodiment, it is preferable that the type of initiator, amount of initiator, polymerization temperature, and so forth are appropriately selected such that the total amount of radicals generated by the polymerization initiator as a proportion relative to the total amount of unreacted monomer remaining in the reaction system is constantly no greater than a certain value.

It is particularly preferable in the present embodiment that in the first half of a period from the start of addition of the polymerization initiator to the end of addition of the polymerization initiator (polymerization initiator addition period), there is at least one instance in which the additive amount of the polymerization initiator per unit time is less than the additive amount of the polymerization initiator per unit time at the start of addition.

Adoption of this method can suppress production of oligomer or low molecular weight component in a latter stage of polymerization and enables improvement of polymerization stability by inhibiting overheating during polymerization.

The chain transfer agent may be any chain transfer agent that is commonly used in radical polymerization and examples thereof include the chain transfer agents disclosed in relation to the production method of the methacrylic resin including the N-substituted maleimide monomer-derived structural unit.

One of these chain transfer agents may be used individually, or two or more of these chain transfer agents may be used together.

These chain transfer agents may be added at any stage, without any specific limitations, so long as the polymerization reaction is in progress.

No specific limitations are placed on the amount of chain transfer agent that is used other than being in a range that enables the desired degree of polymerization under the adopted polymerization conditions. However, when the total amount of monomer used in polymerization is taken to be 100 parts by mass, the amount of the chain transfer agent is preferably 0.05 parts by mass to 1 part by mass.

The methacrylic resin according to the present embodiment that includes the lactone ring structural unit can be obtained by performing a cyclization reaction after completion of the polymerization reaction. Therefore, the polymerization reaction liquid is preferably subjected to the lactone cyclization reaction in a solvent-containing state without removing the polymerization solvent therefrom.

The copolymer obtained through polymerization is heat treated to cause a cyclocondensation reaction between a hydroxy group and an ester group present in the molecular chain of the copolymer and thereby form a lactone ring structure.

Heat treatment for formation of the lactone ring structure may be performed, for example, using a reaction apparatus including a vacuum device or devolatilization device for removal of alcohol that may be produced as a by-product of cyclocondensation, or an extruder including a devolatilization device.

In formation of the lactone ring structure, the heat treatment may be performed in the presence of a cyclocondensation catalyst to promote the cyclocondensation reaction.

Specific examples of cyclocondensation catalysts that can be used include monoalkyl, dialkyl, and trialkyl esters of phosphorus acid such as methyl phosphite, ethyl phosphite, phenyl phosphite, dimethyl phosphite, diethyl phosphite, diphenyl phosphite, trimethyl phosphite, and triethyl phosphite; and monoalkyl, dialkyl, and trialkyl esters of phosphoric acid such as methyl phosphate, ethyl phosphate, 2-ethylhexyl phosphate, octyl phosphate, isodecyl phosphate, lauryl phosphate, stearyl phosphate, isostearyl phosphate, dimethyl phosphate, diethyl phosphate, di-2-ethylhexyl phosphate, diisodecyl phosphate, dilauryl phosphate, distearyl phosphate, diisostearyl phosphate, trimethyl phosphate, triethyl phosphate, triisodecyl phosphate, trilauryl phosphate, tristearyl phosphate, and triisostearyl phosphate.

One of these cyclocondensation catalysts may be used individually, or two or more of these cyclocondensation catalysts may be used together.

Although the amount of cyclocondensation catalyst that is used is not specifically limited, the amount of the cyclocondensation catalyst relative to 100 parts by mass of the methacrylic resin is, for example, preferably 0.01 parts by mass to 3 parts by mass, and more preferably 0.05 parts by mass to 1 part by mass.

Using 0.01 parts by mass or more of a catalyst is effective for improving the rate of the cyclocondensation reaction, whereas using 3 parts by mass or less of a catalyst is effective for preventing coloring of the resultant polymer and polymer crosslinking that then makes melt molding difficult.

The timing of addition of the cyclocondensation catalyst is not specifically limited. For example, the cyclocondensation catalyst may be added in an initial stage of the cyclocondensation reaction, may be added partway through the reaction, or may be added both in the initial stage and partway through the reaction.

In a situation in which the cyclocondensation reaction is carried out in the presence of a solvent, devolatilization is preferably carried out concurrently with the reaction.

Although no specific limitations are placed on the device used in a situation in which the cyclocondensation reaction and a devolatilization step are carried out concurrently, it is preferable to use a devolatilization device comprising a heat exchanger and a devolatilization tank, a vented extruder, or an apparatus in which a devolatilization device and an extruder are arranged in series, and more preferable to use a vented twin-screw extruder.

The vented twin-screw extruder is preferably a vented extruder equipped with a plurality of vent ports.

In a situation in which a vented extruder is used, the reaction treatment temperature is preferably 150° C. to 350° C., and more preferably 200° C. to 300° C. A reaction treatment temperature of 150° C. or higher is effective for preventing inadequate cyclocondensation reaction and excessive residual volatile content, whereas a reaction treatment temperature of 350° C. or lower is effective for inhibiting coloring or decomposition of the resultant polymer.

Moreover, in a situation in which a vented extruder is used, the degree of vacuum therein is preferably 10 Torr to 500 Torr, and more preferably 10 Torr to 300 Torr. Volatile content has a low tendency to remain when the degree of vacuum is 500 Torr or less, whereas industrial implementation is relatively simple when the degree of vacuum is 10 Torr or more.

When a cyclocondensation reaction is performed as described above, an alkaline earth metal and/or amphoteric metal salt of an organic acid is preferably added in pelletization to deactivate residual cyclocondensation catalyst.

Examples of the alkaline earth metal and/or amphoteric metal salt of an organic acid include calcium acetyl acetate, calcium stearate, zinc acetate, zinc octanoate, and zinc 2-ethylhexanoate.

After the cyclocondensation reaction step is completed, the methacrylic resin is melted and extruded as strands from an extruder equipped with a porous die, and is then pelletized by cold cutting, hot cutting in air, strand cutting in water, or under water cutting.

The following describes a preferable methacrylic resin according to the present embodiment.

In one preferable example that may be adopted in the present embodiment, the composition is produced after mixing two or more types of methacrylic resins that include at least a structure derived from a monomer represented by the previously shown formula (4) as a framework, but differ in terms of weight average molecular weight and stereoregularity.

Herein, the stereoregularity of a methacrylic resin is expressed by a ratio (S/H) of the integrated intensity (S) of a syndiotactic fraction (rr) relative to the integrated intensity (H) of a heterotactic fraction (mr) among methacrylic acid ester monomer-derived structural units of the methacrylic resin, as determined by $^1$H-NMR measurement.

In the present embodiment, in a situation in which two or more types of methacrylic resins are mixed in production, the weight average molecular weight (Mw) of each of the methacrylic resins, as measured using a differential refractive index detector, may be freely selected from a range of 70,000 to 800,000.

In the case of a methacrylic resin having a low weight average molecular weight (Mw) (hereinafter, also referred to as a "low molecular weight component"), the weight average molecular weight thereof is preferably 70,000 to 150,000, and more preferably 100,000 to 150,000. Moreover, the S/H ratio thereof used as an indicator of stereoregularity is preferably 1.10 to 1.40.

In the case of a methacrylic resin having a high weight average molecular weight (Mw) (hereinafter, also referred to as a "high molecular weight component"), the weight average molecular weight thereof is preferably 200,000 to 800,000, and more preferably 220,000 to 600,000. Moreover, the S/H ratio thereof used as an indicator of stereoregularity is preferably 1.30 to 1.50.

In the present embodiment, the mixing ratio of the low molecular weight component and the high molecular weight component is not specifically limited and can be appropriately selected from a range of 5 parts by mass to 95 parts by mass of the low molecular weight component and 95 parts by mass to 5 parts by mass of the high molecular weight component.

Through mixing of two or more types of methacrylic resins as described above, it is possible to provide a resin composition that is suitable for optical films and other molded products that are subjected to surface shaping treatment by knurling or the like.

No specific limitations are placed on the method by which two or more types of methacrylic resins having different weight average molecular weights (Mw) and stereoregularity are mixed in the present embodiment. Examples of methods that can be adopted include a method in which liquid-phase mixing of a solution containing two or more types of polymerized products that are obtained through the polymerization reaction described above and have different weight average molecular weights is performed, and then treatment by a devolatilization step or precipitation treatment through addition of a poor solvent is performed; and a method in which mixing is performed using a melt-kneader such as an extruder. Particularly in a situation in which a methacrylic resin having a high molecular weight is used, it is preferable to adopt the method in which liquid-phase mixing of a solution containing two or more types of polymerized products obtained through polymerization reaction is performed, and then treatment by a devolatilization step or precipitation treatment through addition of a poor solvent is performed.

A methacrylic resin according to the present embodiment preferably includes at least one cyclic structural unit selected from the group consisting of an N-substituted maleimide monomer-derived structural unit, a glutarimide-based structural unit, and a lactone ring structural unit. Of such cyclic structural units, it is particularly preferable that the methacrylic resin includes an N-substituted maleimide monomer-derived structural unit in terms that a high degree of control of optical properties such as the photoelastic coefficient can be easily achieved without blending with another thermoplastic resin.

—Other Thermoplastic Resins—

Another thermoplastic resin may be compounded in production of the methacrylic resin composition according to the present embodiment with the aim of adjusting birefringence or improving flexibility, so long as the objectives of the present embodiment are not impeded.

Examples of other thermoplastic resins that can be used include polyacrylates such as polybutyl acrylate; aromatic vinyl resins such as styrene polymers (for example, polystyrene, styrene-methyl methacrylate copolymer, styrene-butyl acrylate copolymer, styrene-acrylonitrile copolymer, and acrylonitrile-butadiene-styrene block copolymer); acrylic rubber particles having a 3 or 4 layer structure described in JP S59-202213 A, JP S63-27516 A, JP S51-129449 A, and JP S52-56150 A; rubbery polymers disclosed in JP S60-17406 B and JP H8-245854 A; and methacrylic rubber-containing graft copolymer particles obtained by multi-step polymerization described in WO 2014-002491 A1.

Of these other thermoplastic resins, from a viewpoint of obtaining good optical properties and mechanical properties, it is preferable to use a styrene-acrylonitrile copolymer or rubber-containing graft copolymer particles having a grafted portion in a surface layer thereof with a chemical composition that is compatible with the methacrylic resin including the structural unit (X) having a cyclic structure-containing main chain.

The average particle diameter of acrylic rubber particles, methacrylic rubber-containing graft copolymer particles, or a rubbery polymer such as described above is preferably 0.03 μm to 1 μm, and more preferably 0.05 to 0.5 μm from a viewpoint of improving impact strength, optical properties, and so forth of a film obtained using the methacrylic resin composition according to the present embodiment.

The content of other thermoplastic resins relative to 100 parts by mass of the methacrylic resin is preferably 0 parts by mass to 50 parts by mass, and more preferably 0 parts by mass to 25 parts by mass.

—Ultraviolet Absorber—

Although no specific limitations are placed on ultraviolet absorbers that can be used, an ultraviolet absorber having a maximum absorption wavelength in a range of 280 nm to 380 nm is preferable. Examples of ultraviolet absorbers that can be used include benzotriazole compounds, benzotriazine compounds, benzophenone compounds, oxybenzophenone compounds, benzoate compounds, phenolic compounds, oxazole compounds, cyanoacrylate compounds, and benzoxazinone compounds.

One of these ultraviolet absorbers may be used individually, or two or more of these ultraviolet absorbers may be used together. By using two types of ultraviolet absorbers having different structures, ultraviolet light can be absorbed over a wider wavelength region.

Examples of benzotriazole compounds that can be used include 2,2'-methylenebis[4-(1,1,3,3-tetramethylbutyl)-6-(2H-benzotriazol-2-yl)phenol], 2-(3,5-di-tert-butyl-2-hydroxyphenyl)-5-chlorobenzotriazole, 2-(2H-benzotriazol-2-yl)-p-cresol, 2-(2H-benzotriazol-2-yl)-4,6-bis(1-methyl-1-phenylethyl)phenol, 2-benzotriazol-2-yl-4,6-di-tert-butylphenol, 2-[5-chloro(2H)-benzotriazol-2-yl]-4-methyl-6-t-butylphenol, 2-(2H-benzotriazol-2-yl)-4,6-di-t-butylphenol, 2-(2H-benzotriazol-2-yl)-4-(1,1,3,3-tetramethylbutyl)phenol, 2-(2H-benzotriazol-2-yl)-4-methyl-6-(3,4,5,6-tetrahydrophthalimidylmethyl)phenol, methyl 3-(3-(2H-benzotriazol-2-yl)-5-t-butyl-4-hydroxyphenyl)propionate/polyethylene glycol 300 reaction product, 2-(2H-benzotriazol-2-yl)-6-(linear/branched dodecyl)-4-methylphenol, 2-(5-methyl-2-hydroxyphenyl)benzotriazole, 2-[2-hydroxy-3,5-bis(α,α-dimethylbenzyl)phenyl]-2H-benzotriazole, and 3-(2H-benzotriazol-2-yl)-5-(1,1-dimethylethyl)-4-hydroxy-C7-9 branched/linear alkyl esters.

Of these benzotriazole compounds, benzotriazole compounds having a molecular weight of 400 or more are preferable. Examples of such benzotriazole compounds that are commercially available products include Kemisorb® 2792 (Kemisorb is a registered trademark in Japan, other countries, or both; produced by Chemipro Kasei Kaisha, Ltd.), ADK STAB® LA31 (ADK STAB is a registered trademark in Japan, other countries, or both; produced by Adeka Corporation), and TINUVIN® 234 (TINUVIN is a registered trademark in Japan, other countries, or both; produced by BASF).

Examples of benzotriazine compounds that can be used include 2-mono(hydroxyphenyl)-1,3,5-triazine compounds, 2,4-bis(hydroxyphenyl)-1,3,5-triazine compounds, and 2,4,6-tris(hydroxyphenyl)-1,3,5-triazine compounds. Specific examples include 2,4-diphenyl-6-(2-hydroxy-4-methoxyphenyl)-1,3,5-triazine, 2,4-diphenyl-6-(2-hydroxy-4-ethoxyphenyl)-1,3,5-triazine, 2,4-diphenyl-6-(2-hydroxy-4-propoxyphenyl)-1,3,5-triazine, 2,4-diphenyl-6-(2-hydroxy-4-butoxyphenyl)-1,3,5-triazine, 2,4-diphenyl-6-(2-hydroxy-4-butoxyphenyl)-1,3,5-triazine, 2,4-diphenyl-6-(2-hydroxy-4-hexyloxyphenyl)-1,3,5-triazine, 2,4-diphenyl-6-(2-hydroxy-4-octyloxyphenyl)-1,3,5-triazine, 2,4-diphenyl-6-(2-hydroxy-4-dodecyloxyphenyl)-1,3,5-triazine, 2,4-diphenyl-6-(2-hydroxy-4-benzyloxyphenyl)-1,3,5-triazine, 2,4-diphenyl-6-(2-hydroxy-4-butoxyethoxy)-1,3,5-triazine, 2,4-bis(2-hydroxy-4-butoxyphenyl)-6-(2,4-dibutoxyphenyl)-1,3,5-triazine, 2,4,6-tris(2-hydroxy-4-methoxyphenyl)-1,3,5-triazine, 2,4,6-tris(2-hydroxy-4-ethoxyphenyl)-1,3,5-triazine, 2,4,6-tris(2-hydroxy-4-propoxyphenyl)-1,3,5-triazine, 2,4,6-tris(2-hydroxy-4-butoxyphenyl)-1,3,5-triazine, 2,4,6-tris(2-hydroxy-4-hexyloxyphenyl)-1,3,5-triazine, 2,4,6-tris(2-hydroxy-4-octyloxyphenyl)-1,3,5-triazine, 2,4,6-tris(2-hydroxy-4-dodecyloxyphenyl)-1,3,5-triazine, 2,4,6-tris(2-hydroxy-4-benzyloxyphenyl)-1,3,5-triazine, 2,4,6-tris(2-hydroxy-4-ethoxyethoxyphenyl)-1,3,5-triazine, 2,4,6-tris(2-hydroxy-4-butoxyethoxyphenyl)-1,3,5-triazine, 2,4,6-tris(2-hydroxy-4-propoxyethoxyphenyl)-1,3,5-triazine, 2,4,6-tris(2-hydroxy-4-methoxycarbonylpropyloxyphenyl)-1,3,5-triazine, 2,4,6-tris(2-hydroxy-4-ethoxycarbonylethyloxyphenyl)-1,3,5-triazine, 2,4,6-tris(2-hydroxy-4-(1-(2-ethoxyhexyloxy)-1-oxopropan-2-yloxy)phenyl)-1,3,5-triazine, 2,4,6-tris(2-hydroxy-3-methyl-4-methoxyphenyl)-1,3,5-triazine, 2,4,6-tris(2-hydroxy-3-methyl-4-ethoxyphenyl)-1,3,5-triazine, 2,4,6-tris(2-hydroxy-3-methyl-4-propoxyphenyl)-1,3,5-triazine, 2,4,6-tris(2-hydroxy-3-methyl-4-butoxyphenyl)-1,3,5-triazine, 2,4,6-tris(2-hydroxy-3-methyl-4-hexyloxyphenyl)-1,3,5-triazine, 2,4,6-tris(2-hydroxy-3-methyl-4-octyloxyphenyl)-1,3,5-triazine, 2,4,6-tris(2-hydroxy-3-methyl-4-dodecyloxyphenyl)-1,3,5-triazine, 2,4,6-tris(2-hydroxy-3-methyl-4-benzyloxyphenyl)-1,3,5-triazine, 2,4,6-tris(2-hydroxy-3-methyl-4-ethoxyethoxyphenyl)-1,3,5-triazine, 2,4,6-tris(2-hydroxy-3-methyl-4-butoxyethoxyphenyl)-1,3,5-triazine, 2,4,6-tris(2-hydroxy-3-methyl-4-propoxyethoxyphenyl)-1,3,5-triazine, 2,4,6-tris(2-hydroxy-3-methyl-4-methoxycarbonylpropyloxyphenyl)-1,3,5-triazine, 2,4,6-tris(2-hydroxy-3-methyl-4-ethoxycarbonylethyloxyphenyl)-1,3,5-triazine, and 2,4,6-tris(2-hydroxy-3-methyl-4-(1-(2-ethoxyhexyloxy)-1-oxopropan-2-yloxy)phenyl)-1,3,5-triazine.

Commercially available products such as Kemisorb 102 (produced by Chemipro Kasei Kaisha, Ltd.), LA-F70 (produced by Adeka Corporation), LA-46 (produced by Adeka Corporation), TINUVIN 405 (produced by BASF), TINUVIN 460 (produced by BASF), TINUVIN 479 (produced by BASF), and TINUVIN 1577FF (produced by BASF) may be used as these benzotriazine compounds.

Of these benzotriazine compounds, an ultraviolet absorber having a 2,4-bis(2,4-dimethylphenyl)-6-[2-hydroxy-4-(3-alkyloxy-2-hydroxypropyloxy)-5-α-cumylphenyl]-s-triazine framework ("alkyloxy" refers to a long chain alkyloxy group such as an octyloxy, nonyloxy, or decyloxy group) is more preferable in terms of having high acrylic resin compatibility and excellent ultraviolet absorption properties.

Particularly from a viewpoint of resin compatibility and volatility during heating, the ultraviolet absorber is preferably a benzotriazole compound having a molecular weight of 400 or more or a benzotriazine compound, and from a viewpoint of inhibiting decomposition of the ultraviolet absorber under heating during extrusion, the ultraviolet absorber is particularly preferably a benzotriazine compound.

The melting point (Tm) of the ultraviolet absorber is preferably 80° C. or higher, more preferably 100° C. or higher, further preferably 130° C. or higher, and even more preferably 160° C. or higher.

The weight reduction rate of the ultraviolet absorber under heating from 23° C. to 260° C. at a rate of 20° C./min is preferably 50% or less, more preferably 30% or less, further preferably 15% or less, even more preferably 10% or less, and particularly preferably 5% or less.

The amount of the ultraviolet absorber is not specifically limited so long as the disclosed effects can be displayed without impairing heat resistance, damp heat resistance, thermal stability, and molding properties, but relative to 100 parts by mass of the methacrylic resin, is preferably 0.1 parts by mass to 5 parts by mass, more preferably 0.2 parts by mass to 4 parts by mass, further preferably 0.25 parts by mass to 3 parts by mass, and even more preferably 0.3 parts by mass to 3 parts by mass. When the amount of the ultraviolet absorber is within any of the ranges set forth above, an excellent balance of ultraviolet absorption performance, film molding properties, thin film compatibility, and so forth can be obtained.

—Antioxidant—

At least one antioxidant selected from hindered phenol antioxidants, phosphoric antioxidants, sulfuric antioxidants, and the like is preferably added to the methacrylic resin composition according to the present embodiment so that the properties of the methacrylic resin according to the present embodiment are expressed.

One of these antioxidants may be used, or two or more of these antioxidants may be used in combination.

Specific examples of hindered phenol antioxidants that can be used include, but are not specifically limited to, pentaerythritol tetrakis[3-(3,5-di-tert-butyl-4-hydroxyphenyl)propionate], thiodiethylene bis[3-(3,5-di-tert-butyl-4-hydroxyphenyl)propionate], octadecyl-3-(3,5-di-tert-butyl-4-hydroxyphenyl)propionate, 3,3',3",5,5',5"-hexa-tert-butyl-a,a',a"-(mesitylene-2,4,6-triyl)tri-p-cresol, 4,6-bis(octylthiomethyl)-o-cresol, 4,6-bis(dodecylthiomethyl)-o-cresol, ethylenebis(oxyethylene)bis[3-(5-tert-butyl-4-hydroxy-m-tolyl)propionate], hexamethylene bis[3-(3,5-di-tert-butyl-4-hydroxyphenyl)propionate], 1,3,5-tris(3,5-di-tert-butyl-4-hydroxybenzyl)-1,3,5-triazine-2,4,6(1H,3H,5H)-trione, 1,3,5-tris[(4-tert-butyl-3-hydroxy-2,6-xylene)methyl]-1,3,5-triazine-2,4,6(1H, 3H,5H)-trione, 2,6-di-tert-butyl-4-(4,6-bis(octylthio)-1,3,5-triazin-2-ylamine)phenol, 2-[1-(2-hydroxy-3,5-di-tert-pentylphenyl)ethyl]-4,6-di-tert-pentylphenyl acrylate, and 2-tert-butyl-4-methyl-6-(2-hydroxy-3-tert-butyl-5-methylbenzyl)phenyl acrylate.

In particular, pentaerythritol tetrakis[3-(3,5-di-tert-butyl-4-hydroxyphenyl)propionate], octadecyl-3-(3,5-di-t-butyl-4-hydroxyphenyl)propionate, and 2-[1-(2-hydroxy-3,5-di-tert-pentylphenyl)ethyl]-4,6-di-tert-pentylphenyl acrylate are preferable.

Commercially available hindered phenol antioxidants may be used as these hindered phenol antioxidants. Examples of such commercially available hindered phenol antioxidants include, but are not specifically limited to, Irganox® 1010 (Irganox is a registered trademark in Japan, other countries, or both; pentaerythritol tetrakis[3-(3,5-di-t-butyl-4-hydroxyphenyl)propionate]; produced by BASF), Irganox 1076 (octadecyl-3-(3,5-di-t-butyl-4-hydroxyphenyl)propionate; produced by BASF), Irganox 1330 (3,3',3",5,5',5"-hexa-t-butyl-a,a',a"-(mesitylene-2,4,6-triyl)tri-p-cresol; produced by BASF), Irganox 3114 (1,3,5-tris(3,5-di-t-butyl-4-hydroxybenzyl)-1,3,5-triazine-2,4,6(1H,3H, 5H)-trione; produced by BASF), Irganox 3125 (produced by BASF), ADK STAB AO-60 (pentaerythritol tetrakis[3-(3,5-di-t-butyl-4-hydroxyphenyl)propionate]; produced by Adeka Corporation), ADK STAB AO-80 (3,9-bis{2-[3-(3-t-butyl-4-hydroxy-5-methylphenyl)propionyloxy]-1,1-dimeth ylethyl}-2,4,8,10-tetraoxaspiro[5.5]undecane; produced by Adeka Corporation), Sumilizer® BHT (Sumilizer is a registered trademark in Japan, other countries, or both; produced by Sumitomo Chemical Co., Ltd.), Cyanox® 1790 (Cyanox is a registered trademark in Japan, other countries, or both; produced by Cytec Solvay Group), Sumilizer GA-80 (produced by Sumitomo Chemical Co., Ltd.), Sumilizer GS (2-[1-(2-hydroxy-3,5-di-tert-pentylphenyl)ethyl]-4,6-di-tert-pentylphenyl acrylate; produced by Sumitomo Chemical Co., Ltd.), Sumilizer GM (2-tert-butyl-4-methyl-6-(2-hydroxy-3-tert-butyl-5-methylbenzyl)phenyl acrylate; produced by Sumitomo Chemical Co., Ltd.), and vitamin E (produced by Eisai Co., Ltd.).

Of these commercially available phenolic antioxidants, Irganox 1010, Irganox 1076, ADK STAB AO-60, ADK STAB AO-80, Sumilizer GS, and the like are preferable in terms of thermal stability imparting effect with respect to the resin.

One of these hindered phenol antioxidants may be used individually, or two or more of these hindered phenol antioxidants may be used together.

Examples of phosphoric antioxidants that can be used include those classified as phosphites and phosphonites.

Specific examples of phosphites that can be used as phosphoric antioxidants include, but are not specifically limited to, tris(2,4-di-t-butylphenyl) phosphite, tris(2,6-di-t-butylphenyl) phosphite, tris(2,4-di-t-butyl-5-methylphenyl) phosphite, bis(2,4-di-t-butyl-6-methylphenyl)ethyl phosphite, 2,2'-methylenebis(4,6-di-t-butylphenyl)octyl phosphite, bis(2,6-di-t-butyl-4-methylphenyl)pentaerythritol diphosphite, and cyclic neopentanetetraylbis(2,6-di-t-butyl-4-methylphenyl) phosphite.

Commercially available phosphoric antioxidants may be used, examples of which include Irgafos 168 (tris(2,4-di-t-butylphenyl) phosphite; produced by BASF), Irgafos 12 (tris[2-[[2,4,8,10-tetra-t-butyldibenzo[d,f][1,3,2]dioxaphosphepin-6-yl]oxy]ethyl]amine; produced by BASF), Irgafos 38 (bis(2,4-di-tert-butyl-6-methylphenyl)ethyl phosphite; produced by BASF), ADK STAB HP-10 (2,2'-methylenebis (4,6-di-tert-butylphenyl)octyl phosphite; produced by Adeka Corporation), ADK STAB PEP24G (cyclic neopentanetetraylbis(2,4-di-tert-butylphenyl) phosphite; produced by Adeka Corporation), ADK STAB PEP36 (bis(2,6-di-t-butyl-4-methylphenyl)pentaerythritol diphosphite; produced by Adeka Corporation), ADK STAB PEP36A (bis(2, 6-di-t-butyl-4-methylphenyl)pentaerythritol diphosphite; produced by Adeka Corporation), ADK STAB PEP-8 (cyclic neopentanetetraylbis(2,4-di-tert-butylphenyl) phosphite; produced by Adeka Corporation), and Sumilizer GP (6-[3-(3-t-butyl-4-hydroxy-5-methylphenyl)propoxy]-2,4,8,10-tetra-t-butyldibenzo[d,f][1,3,2]dioxaphophepin; produced by Sumitomo Chemical Co., Ltd.).

Examples of phosphonites that can be used as phosphoric antioxidants include tetrakis(2,4-di-tert-butylphenyl)-4,4'-biphenylenediphosphonite and tetrakis(2,4-di-tert-butyl-5-methylphenyl)-4,4'-biphenylenediphosphonite.

Commercially available phosphonites may be used as the phosphoric antioxidant, examples of which include Hostanox® P-EPQ (Hostanox is a registered trademark in Japan, other countries, or both; tetrakis(2,4-di-tert-butylphenyl)-4, 4'-biphenylenediphosphonite; produced by Clariant Co., Ltd.) and GSY P101 (tetrakis(2,4-di-t-butyl-5-methylphenyl)-4,4'-biphenylenediphosphonite; produced by Sakai Chemical Industry Co., Ltd.).

Of these commercially available phosphoric antioxidants, ADK STAB PEP-36, ADK STAB PEP-36A, Sumilizer GP, GSY P101, and the like are preferable in terms of thermal stability imparting effect with respect to the resin.

One of these phosphoric antioxidants may be used individually, or two or more of these phosphoric antioxidants may be used together.

Specific examples of sulfuric antioxidants that can be used include, but are not specifically limited to, 2,4-bis (dodecylthiomethyl)-6-methylphenol (Irganox 1726 produced by BASF), Irganox 1520L (produced by BASF), 2,2-bis[[3-(dodecylthio)-1-oxopropoxy]methyl]propan-1,3-diyl bis[3-(dodecylthio)propionate] (ADK STAB AO-4125 produced by Adeka Corporation), 2,2-bis[[3-(dodecylthio)-

1-oxopropoxy]methyl]propan-1,3-diyl bis[3-(dodecylthio) propionate] (KEMINOX® PLS (KEMINOX is a registered trademark in Japan, other countries, or both) produced by Chemipro Kasei Kaisha, Ltd.), and di(tridecyl)-3,3'-thiodipropionate (AO-503 produced by Adeka Corporation).

Of these commercially available sulfuric antioxidants, ADK STAB AO-4125, KEMINOX PLS, and the like are preferable in terms of thermal stability imparting effect with respect to the resin.

One of these sulfuric antioxidants may be used individually, or two or more of these sulfuric antioxidants may be used together.

Although the content of the antioxidant can be any amount that enables an effect of thermal stability improvement, excessively high antioxidant content may lead to problems such as bleed-out during processing. Accordingly, the content of the antioxidant relative to 100 parts by mass of the methacrylic resin is preferably 5 parts by mass or less, more preferably 3 parts by mass or less, further preferably 1 part by mass or less, even more preferably 0.8 parts by mass or less, even further preferably 0.01 parts by mass to 0.8 parts by mass, and particularly preferably 0.01 parts by mass to 0.5 parts by mass.

—Other Additives—

The methacrylic resin composition according to the present embodiment may contain other additives to the extent that the effects according to the present embodiment are not significantly lost.

Examples of other additives that can be used include, but are not specifically limited to, inorganic fillers; pigments such as iron oxide; lubricants and release agents such as stearic acid, behenic acid, zinc stearate, calcium stearate, magnesium stearate, and ethylene bis stearamide; softeners and plasticizers such as paraffinic process oils, naphthenic process oils, aromatic process oils, paraffin, organic polysiloxanes, and mineral oils; higher alcohols such as cetyl alcohol and stearyl alcohol; release agents such as glycerin higher fatty acid esters (for example, stearic acid monoglyceride and stearic acid diglyceride); flame retardants; antistatic agents; reinforcers such as organic fiber, glass fiber, carbon fiber, and metal whisker; colorants; other additives; and mixtures of any of the preceding examples.

The following provides a detailed description of properties of the methacrylic resin composition according to the present embodiment.

—Weight Average Molecular Weight (Mw)—

The weight average molecular weight (Mw) of the methacrylic resin composition according to the present embodiment determined as a polymethyl methacrylate equivalent molecular weight through measurement by gel permeation chromatography (GPC) using a differential refractive index detector is preferably 120,000 to 200,000, more preferably 120,000 to 170,000, and even more preferably 120,000 to 150,000. A weight average molecular weight (Mw) in any of the ranges set forth above is preferable in terms that an excellent balance of mechanical strength and molding properties can be achieved.

—Vicat Softening Temperature—

The Vicat softening temperature (Tvicat) of the methacrylic resin composition according to the present embodiment is 120° C. to 160° C., preferably 120° C. to 150° C., and more preferably 120° C. to 140° C.

The Vicat softening temperature (Tvicat) can be determined through measurement of a specimen of 4 mm in thickness in accordance with ISO 306.

Measurement of the Vicat softening temperature is carried out by determining the temperature at which deformation of the resin due to heat starts to occur. Although the Vicat softening temperature is defined as the temperature of the specimen at which a needle having a needle tip area of 1 $mm^2$ sinks to a depth of 1 mm within the specimen, the Vicat softening temperature is normally taken to be the temperature of a heat transfer medium that is used in measurement.

This indicator is influenced not only by the glass transition temperature and melting point of the resin, but also by the molecular weight and molecular weight distribution of the resin. Moreover, this indicator is expected to be strongly influenced by the glass transition temperature distribution with respect to softening behavior of the resin, and is considered to be a useful indicator when the resin is heated and softened for secondary processing (inclusive of surface shaping processing by heating that is a subject of the present disclosure).

As a result of the Vicat softening temperature of the methacrylic resin composition being 120° C. or higher, the heat resistance required in recent years for lens molded products and film molded product optical films for liquid-crystal displays can be easily obtained.

On the other hand, if the Vicat softening temperature of a methacrylic resin composition is higher than 160° C., it is necessary to adopt a rather high temperature during melt processing, which may lead to thermal decomposition of resin and the like, and thus it may be difficult to obtain a good quality product by melt processing.

In the case of a resin or resin composition that has the same glass transition temperature as another resin or resin composition, but has a higher Vicat softening temperature, this indicates that there is a difference in viscoelastic behavior at temperatures equal to or lower than the glass transition temperature. Therefore, in a situation in which a resin is heated and the surface of a molded product is shaped such as in the present embodiment, among resins or resin compositions having the same glass transition temperature, a resin or resin composition having a higher Vicat softening temperature is preferable in terms that better shape replicability can be obtained.

—Stereoregularity—

In the methacrylic resin according to the present embodiment having a cyclic structure-containing main chain and the methacrylic resin composition according to the present embodiment containing this methacrylic resin, the stereoregularity of methacrylic acid ester monomer-derived structural units is expressed by a ratio (S/H) of the integrated intensity (S) of a syndiotactic fraction (rr) relative to the integrated intensity (H) of a heterotactic fraction (mr) among methacrylic acid ester monomer-derived structural units, as determined by $^1$H-NMR measurement.

The S/H ratio is 1.20 to 1.50, preferably 1.25 to 1.50, and more preferably 1.30 to 1.40.

An S/H ratio that is within any of the ranges set forth above is preferable in terms that shape replicability is possible even when the conveyance speed in a surface shaping step of knurling or the like is increased, such as in mass production, and in terms that durable protrusions and recesses can be shaped.

In a conventionally known method for improving the stereoregularity of methacrylic acid ester monomer-derived structural units in a methacrylic resin, low-temperature radical polymerization or anionic polymerization is adopted.

However, there is almost no conventional knowledge relating to the stereoregularity of methacrylic acid ester monomer-derived structural units in a copolymer obtained through radical polymerization with one or more other monomers, and findings in relation to such stereoregularity have been made for the first time through investigation by the inventors.

This investigation by the inventors revealed that the stereoregularity of a copolymer varies depending on the type and content of other copolymerizable monomers used in polymerization, and also varies depending on the addition method in polymerization of copolymerizable monomers used in polymerization.

Moreover, the inventors discovered that surface shaping properties of a molded product by knurling or the like can be improved by mixing two or more types of methacrylic resins that each have a cyclic structure-containing main chain, but differ in terms of weight average molecular weight and stereoregularity.

The stereoregularity of methacrylic acid ester monomer-derived structural units in a methacrylic resin having a cyclic structure-containing main chain and a methacrylic resin composition containing this methacrylic resin can be measured by calculating the proportions of triad tacticities by $^1$H-NMR measurement.

Specifically, the triad tacticities can be measured by the following method. In the method, a sample is dissolved in chloroform and is then measured by $^1$H-NMR measurement using, for example, a 400 MHz NMR spectrometer (for example, an NMR spectrometer produced by Bruker Corporation). The integrated values for peaks near $\delta$ 1.2 ppm, $\delta$ 1.0 ppm, and $\delta$ 0.8 ppm are respectively taken to be the proportions of isotactic triads, heterotactic triads, and syndiotactic triads.

More specifically, the triad tacticities can be obtained by a method described in the subsequent EXAMPLES section.

—Methanol-Soluble Content—

The amount of methanol-soluble content in the methacrylic resin composition according to the present embodiment as a proportion relative to 100 mass %, in total, of methanol-soluble content and methanol-insoluble content, is 5 mass % or less, preferably 4.5 mass % or less, more preferably 4 mass % or less, further preferably 3.5 mass % or less, preferably 3 mass % or less, and more preferably 2.5 mass % or less.

It is preferable that the proportion of methanol-soluble content is 5 mass % or less in terms that even when the conveyance speed in a surface shaping step of knurling or the like is increased, such as in mass production, excellent release properties and shape replicability can be achieved and durable protrusions and recesses can be shaped.

The methanol-soluble content and methanol-insoluble content refer to components obtained by dissolving the methacrylic resin composition in chloroform, dripping the resultant solution into an excess of methanol to cause re-precipitation, separating a filtrate and a filtration residue, and then drying the obtained filtrate and filtration residue. Specifically, the methanol-soluble content and the methanol-insoluble content can be obtained by a method described in the subsequent EXAMPLES section.

Examples of methods that can be used to adjust the amount of methanol-soluble content to within any of the ranges set forth above include, but are not specifically limited to, a method in which production of oligomer or low-molecular weight product is suppressed by controlling the addition method of monomers and the addition method of polymerization initiator in polymerization.

The methanol-soluble content of the methacrylic resin composition according to the present embodiment may include, for example, unreacted monomer components, oligomer components such as dimers and trimers of these monomers, and low-molecular weight components that have a weight average molecular weight of approximately 1,000 to 15,000 and have a chemical composition such as to be soluble in normal temperature methanol.

In the case of an optical film subjected to surface shaping by knurling or the like, these components are expected migrate relatively easily to the surface of the film, or other molded product, as a result of having high mobility. Consequently, in a situation in which surface shaping treatment is carried out at a relatively high temperature that is equal to or higher than the glass transition temperature, it is expected that release properties from a cutting die may be affected and that cooling and solidification behavior after treatment may also be affected. Therefore, restricting the proportion of methanol-soluble content contained in the methacrylic resin composition to within a specific range can raise the processing stability of surface shaping by knurling or the like.

—Glass Transition Temperature—

The glass transition temperature (Tg) of the methacrylic resin composition according to the present embodiment is preferably higher than 120° C. and no higher than 160° C.

When the glass transition temperature (Tg) of the methacrylic resin composition is higher than 120° C., the heat resistance required in recent years for optical components such as lens molded products, film molded products for liquid-crystal displays, and optical films can be more easily obtained.

On the other hand, when the glass transition temperature (Tg) of a methacrylic resin composition is higher than 160° C., it is necessary to adopt a rather high temperature during melt processing, which tends to facilitate thermal decomposition of resin and the like, and thus it may be difficult to obtain a good quality product by melt processing.

The glass transition temperature (Tg) can be measured in accordance with JIS-K7121.

For example, the glass transition temperature (Tg) (° C.) may be measured as follows. First, specimens are obtained by cutting approximately 10 mg from a sample at four points (four locations) after the sample has been conditioned (left for 1 week at 23° C.) in a standard state (23° C., 65% RH). A DSC curve is then plotted using a differential scanning calorimeter (Diamond DSC produced by PerkinElmer Japan) under a nitrogen gas flow rate of 25 mL/min while heating the specimen from room temperature (23° C.) to 200° C. at 10° C./min (primary heating), holding the specimen at 200° C. for 5 minutes to completely melt the specimen, cooling the specimen from 200° C. to 40° C. at 10° C./min, holding the specimen at 40° C. for 5 minutes, and then reheating the specimen under the same heating conditions (secondary heating). The glass transition temperature (Tg) (° C.) is then measured as the intersection point (mid-point glass transition temperature) of a stair-shaped change section of the DSC curve during the secondary heating and a straight line that is equidistant in a vertical axis direction from each extrapolated baseline. Four points are measured per sample and the arithmetic mean (rounded to nearest whole number beyond the decimal point) is taken to be the measured value.

—Photoelastic Coefficient—

The absolute value of the photoelastic coefficient $C_R$ of the methacrylic resin composition according to the present embodiment including the structural unit (X) having a cyclic structure-containing main chain is preferably $3.0 \times 10^{-12}$ Pa$^{-1}$ or less, more preferably $2.0 \times 10^{-12}$ Pa$^{-1}$ or less, and even more preferably $1.0 \times 10^{-12}$ Pa$^{-1}$ or less.

The photoelastic coefficient is described in various documents (for example, refer to Review of Chemistry, No. 39, 1998 (published by Japan Scientific Societies Press)) and is defined by the following formulae (i-a) and (i-b). The closer the value of the photoelastic coefficient $C_R$ is to zero, the smaller the change in birefringence caused by external force.

$$C_R = |\Delta n|/\sigma_R \qquad \text{(i-a)}$$

$$|\Delta n| = |nx - ny| \qquad \text{(i-b)}$$

(In the above formulae, $C_R$ represents the photoelastic coefficient, $\sigma_R$ represents tensile stress, $|\Delta n|$ represents the absolute value of birefringence, nx represents the refractive index of the tension direction and ny represents the refractive index of an in-plane direction that is perpendicular to the tension direction.)

When the absolute value of the photoelastic coefficient $C_R$ of the methacrylic resin composition according to the present embodiment is $3.0 \times 10^{-12}$ $Pa^{-1}$ or less, in a situation in which the methacrylic resin composition is formed into a film and used in a liquid-crystal display, it is possible to inhibit or prevent phase difference irregularity, reduced contrast at the periphery of the display screen, and light leakage.

The photoelastic coefficient $C_R$ can, more specifically, be determined by a method described in the subsequent EXAMPLES section.

(Production Method of Methacrylic Resin Composition)

No specific limitations are placed on the method by which the methacrylic resin composition according to the present embodiment is produced other than being a method through which a composition that satisfies the requirements of this disclosure can be obtained.

In a situation in which a melt-extrusion method is adopted for producing the methacrylic resin composition according to the present embodiment, it is preferable to adopt a method in which a vented extruder is used to produce the composition while removing as much of residual volatile components as possible.

Moreover, in a situation in which the methacrylic resin composition according to the present embodiment is to be used in a film application or the like, the methacrylic resin composition is preferably produced by also using, for example, a filtration device such as a sintered filter, pleated filter, or leaf disk-type polymer filter having a filtration precision of 1.5 μm to 20 μm in one or more steps selected from a polymerization reaction step, a liquid-liquid separation step, a liquid-solid separation step, a devolatilization step, a pelletization step, and a molding step in order to reduce the amounts of contaminants.

Whichever method is selected, production of the methacrylic resin composition is preferably carried out after reducing the amount of oxygen and moisture as much as possible.

For example, the dissolved oxygen concentration in a polymerization solution in solution polymerization is preferably less than 300 ppm in the polymerization step, and in a production method in which an extruder or the like is used, the oxygen concentration inside the extruder is preferably less than 1 volume %, and more preferably less than 0.8 volume %.

It is recommended that the amount of moisture in the methacrylic resin is adjusted to preferably 1,000 mass ppm or less, and more preferably 500 mass ppm or less.

Values within any of the ranges set forth above are beneficial in terms that it becomes relatively easy to produce a composition that satisfies the requirements of this disclosure.

For example, when a production method using an extruder is adopted, it is preferable that pelletized methacrylic resin used as a raw material is sufficiently dried in advance by heating under vacuum or in dehumidified air to remove as much moisture as possible.

Moreover, in a situation in which any of the various antioxidants or additives described below are compounded in production, it is preferable that the amount of moisture contained in such antioxidants and additives is reduced to as great an extent as possible prior to compounding thereof.

Furthermore, in order to reduce entry of oxygen into the extruder to as great an extent as possible and prevent oxidization of the molten composition, it is preferable that an inert gas, such as nitrogen gas, is caused to flow inside the extruder and that production is carried out using a vented extruder while performing vacuum venting.

In drying of raw materials and the like, the drying temperature is preferably 40° C. to 120° C., and more preferably 70° C. to 100° C.

The degree of vacuum can be selected as appropriate without any specific limitations.

Molten methacrylic resin that has been melt-kneaded is then melt-extruded from a porous die using the extruder and is pelletized.

The pelletization method used during this process may be, for example, hot cutting in air, water ring-type hot cutting, cold cutting, strand cutting in water, under water cutting, or the like.

Of these methods, strand cutting in water is generally more preferable in terms of productivity and pelletizer cost.

The pelletization is more preferably performed under implementable conditions in which the temperature of the molten resin is as low as possible, the residence time from an outlet of the porous die to the surface of cooling water is as short as possible, and the temperature of the cooling water is as high as possible.

For example, the temperature of the molten resin is preferably 240° C. to 300° C., and more preferably 250° C. to 290° C., the residence time from the outlet of the porous die to the surface of the cooling water is preferably 5 seconds or less, and more preferably 3 seconds or less, and the temperature of the cooling water is preferably 30° C. to 80° C., and more preferably 40° C. to 60° C.

As previously described, from a viewpoint of obtaining suitable chemical composition distribution properties in the resin composition, it is preferable in the present embodiment to use two or more types of methacrylic resins that each have the same type of cyclic structure in the main chain thereof, but differ in terms of weight average molecular weight, Vicat softening point, and S/H ratio, and to select the proportion of structural units derived from each monomer, the weight average molecular weight, the Vicat softening point, and the S/H ratio of each methacrylic resin, and the mixing ratio of these methacrylic resins as appropriate, so long as the properties stipulated in the present embodiment are satisfied.

No specific limitations are placed on the method used in the present embodiment to produce a resin composition in which two or more types of methacrylic resins are mixed that have the same type of cyclic structural unit in the main chain thereof, but differ in terms of weight average molecular weight (Mw), Vicat softening point, and S/H ratio. For example, a method involving melt-kneading using an extruder may be adopted.

Details relating to two types of methacrylic resins and details relating to the weight average molecular weight (Mw), S/H ratio, and mixing ratio of a high molecular weight component and a low molecular weight component among these two methacrylic resins may be the same as previously described.

In particular, a situation in which the S/H ratio of a high molecular weight component is greater than the S/H ratio of a low molecular weight component is preferable in terms of enabling stable formation of a protrusion/recess shape at the surface of a film or other molded product by knurling or the like.

As previously described, the method by which two or more types of methacrylic resins are mixed is not specifically limited and examples thereof include a method in which a solution containing two or more types of polymerized products is mixed in liquid-phase and subjected to post-treatment, and a method in which mixing is performed using a melt-kneader, such as an extruder, after pelletization. In particular, a method in which a solution containing two or more types of polymerized products is mixed in liquid-phase and subjected to post-treatment is preferable when a methacrylic resin having a high molecular weight is used.

—Production Method of Molded Product—

The resin composition according to the present embodiment may be used to form a molded product by a commonly known method such as injection molding, sheet molding, blow molding, injection blow molding, inflation film molding, T-die film molding, press molding, extrusion molding, foam molding, or cast molding, and with further use of a molding method for secondary processing such as pressure molding or vacuum molding.

Of these methods, sheet molding, inflation film molding, T-die film molding, and extrusion molding are suitable for forming a sheet or film to obtain an optical sheet or optical film.

For example, the following provides a description of a method of producing a pre-stretching film (unstretched film) and a stretched film using the methacrylic resin composition according to the present embodiment.

The method involves, for example, supplying raw material resin into a single-screw or twin-screw extruder, melt-kneading the raw material resin, subsequently extruding a sheet using a T-die, guiding the sheet on a casting roll, and solidifying the sheet. Next, longitudinal uniaxial stretching may be performed by stretching in the directional of mechanical flow using a pair of rolls having different circumferential speeds, transverse uniaxial stretching may be performed by stretching in a perpendicular direction (TD direction) relative to the direction of mechanical flow, or biaxial stretching may be performed by sequential biaxial stretching using roll stretching and tenter stretching, simultaneous biaxial stretching by tenter stretching, biaxial stretching by tubular stretching, inflation stretching, tenter method sequential biaxial stretching, or the like. Of these methods, sequential biaxial stretching comprising roll stretching and tenter stretching is preferable as this enables the greatest expression of the features of the methacrylic resin composition according to the present embodiment.

The final stretching ratio can be determined in consideration of the heat shrinkage rate of the resultant molded/stretched product. The stretching ratio in at least one direction is preferably 0.1% to 400%, more preferably 10% to 400%, and even more preferably 50% to 350%. When the stretching ratio is less than any of the lower limits set forth above, folding strength tends to be insufficient, and when the stretching ratio is greater than any of the upper limits set forth above, a film cannot be continuously and stably produced because breaking or rupturing frequently occurs during the film production process. By designing within any of the ranges set forth above, it is possible to obtain a preferable stretched molded product in terms of birefringence, heat resistance, and strength.

The stretching temperature is preferably Tvicat−30° C. to Tvicat+50° C. Tvicat (Vicat softening temperature) refers to a value for the resin composition used in production of the film.

In order that the resultant film has good thickness uniformity, the lower limit for the stretching temperature is preferably Tvicat−20° C. or higher, more preferably Tvicat−10° C. or higher, further preferably Tvicat or higher, even more preferably Tvicat+5° C. or higher, and particularly preferably Tvicat+7° C. or higher. Moreover, the upper limit for the stretching temperature is preferably Tvicat+45° C. or lower, and more preferably Tvicat+40° C. or lower.

In a situation in which the film according to the present embodiment is to be used as an optical film, the film is preferably subjected to heat treatment (annealing) or the like after stretching treatment to stabilize optical isotropy and mechanical properties of the film. The heat treatment conditions are not specifically limited and may be selected as appropriate in the same manner as for the conditions of heat treatment performed with respect to conventional and commonly known stretched films. For example, the heat treatment may be performed with a temperature of preferably Tvicat−30° C. to Tvicat+30° C., more preferably Tvicat−30° C. to Tvicat+20° C., and even more preferably Tvicat−15° C. to Tvicat+10° C., for a time of preferably 1 second to 10 minutes, and more preferably 5 seconds to 4 minutes, and with a tension of preferably 0.1 kg/m to 20 kg/m.

Although the thickness of the optical film is not specifically limited, the thickness may be, for example, 1 μm to 250 μm, and is preferably 10 to 100 μm.

The molded product according to the present embodiment preferably includes an embossed section on at least part of either or both of a front surface and a rear surface.

The embossed section may be provided just in proximity to a film edge. The shape of protrusions in the embossed section may be selected as appropriate depending on the objective and application, and may be a circular shape, a polygonal shape such as square shape, diamond shape, or trapezoidal shape, or the like.

The shaped design may differ depending on the thickness of the molded product on which the embossed section is formed. For example, in the case of a 40 μm biaxially stretched film subjected to knurling, the density of protrusions in the embossed section is preferably 50 per $cm^2$ to 200 per $cm^2$, but is not specifically limited to this range.

Moreover, although no specific limitations are placed on the height of protrusions in the embossed section, in the case of a film of 40 μm in thickness, the height of the protrusions is preferably 6 μm to 16 μm, and particularly preferably 8 μm to 14 μm. Also note that the protrusions may each have the same height or may have different heights. The height of the protrusions can be measured by a method described in the subsequent EXAMPLES section.

Although no specific limitations are placed on possible applications for the film, sheet, or other molded product, examples include light guide plates, diffuser plates, quarter-wave plates, half-wave plates, polarizer protective films, viewing angle compensation films, liquid-crystal optical compensation films and other retardation films, display front plates, display base plates, lenses, touch panels, optical waveguides, and the like used in displays such as liquid-crystal displays, plasma displays, organic EL displays, field emission displays, and rear projection televisions. Use in transparent base plates and the like of solar cells is also appropriate.

Examples of molded product applications include household goods, OA equipment, AV equipment, battery fittings, lighting equipment, automobile component applications for tail lamps, meter covers, head lamps, light guide rods, lenses, and so forth, housing applications, sanitary applications as a sanitary ware alternative or the like, and light guide plates, diffuser plates, polarizing plate protective films, quarter-wave plates, half-wave plates, viewing angle control films, liquid-crystal optical compensation film and other retardation films, display front plates, display base plates, lenses, touch panels, and the like used in displays such as liquid-crystal displays, plasma displays, organic EL displays, field emission displays, and rear projection televisions. Use in transparent base plates and the like of solar cells is also appropriate. Other possible applications include those in the fields of optical communication systems, optical switching systems, and optical measurement systems for waveguides, lenses, optical fibers, optical fiber coating materials, LED lenses, lens covers, and so forth. Moreover, use as a modifier for another resin is also possible.

Of such applications, optical components are preferable (particularly optical components having an embossed section on at least part of either or both of a front surface and a rear surface), and optical films are more preferable (particularly optical films having an embossed section on at least part of either or both of a front surface and a rear surface).

Through the methacrylic resin composition according to the present embodiment and the optical component according to the present embodiment, in a situation in which, with regards to production of a molded product for use in the optical field (particularly an optical film) that is subjected to surface shaping treatment, there is progress toward higher line speed, smaller film thickness, and commercialization as an elongated roll, it is still possible to inhibit a decrease in film quality associated with long-term storage or transport. Therefore, according to the present embodiment, it is possible to provide a methacrylic resin composition that can be used to produce an optical film or other molded product for use in the optical field that has excellent surface shaping properties, and to provide an optical component such as an optical film.

EXAMPLES

The following provides a more specific description of the disclosed matter through examples and comparative examples. However, this disclosure is not limited to the following examples.

(1. Analysis of Structural Units)

With respect to methacrylic resins produced in the following production examples and methacrylic resin compositions produced in the following examples and comparative examples, each type of structural unit included therein was identified and the amounts of these structural units were calculated by $^1$H-NMR measurement and $^{13}$C-NMR measurement, unless otherwise specified. The $^1$H-NMR and $^{13}$C-NMR measurement conditions were as follows.

Measurement device: DPX-400 produced by Bruker Corporation
Measurement solvent: $CDCl_3$ or $d_6$-DMSO
Measurement temperature: 40° C.

In the case of a methacrylic resin having a lactone ring structure as the cyclic structure thereof, this structure was confirmed by a method described in JP 2001-151814 A, and in the case of a methacrylic resin having a glutarimide cyclic structure as the cyclic structure thereof, this structure was confirmed by a method described in WO 2012/114718 A1.

<2. Weight Average Molecular Weight (Mw) and Molecular Weight Distribution (Mw/Mn)>

The weight average molecular weight (Mw) and number average molecular weight (Mn) of methacrylic resins produced in the following production examples and methacrylic resin compositions produced in the following examples and comparative examples were measured using the following device and conditions.

Measurement device: Gel permeation chromatograph (HLC-8320GPC) produced by Tosoh Corporation
Measurement Conditions
Column: TSK guard column Super H-H×1, TSK gel Super HM-M×2, TSK gel Super H2500×1; connected in series in this order
Column temperature: 40° C.
Developing solvent: Tetrahydrofuran, 0.6 mL/min flow rate, 0.1 g/L of 2,6-di-t-butyl-4-methylphenol (BHT) added as internal standard
Detector: Refractive index (RI) detector
Detection sensitivity: 3.0 mV/min
Sample: Solution of 0.02 g of methacrylic resin or methacrylic resin composition in 20 mL of tetrahydrofuran
Injection amount: 10 μL
Standard samples for calibration curve: Following 10 types of polymethyl methacrylate (PMMA Calibration Kit M-M-10 produced by Polymer Laboratories Ltd.) of differing molecular weight each having a known monodisperse weight peak molecular weight
Weight peak molecular weight (Mp)
Standard sample 1: 1,916,000
Standard sample 2: 625,500
Standard sample 3: 298,900
Standard sample 4: 138,600
Standard sample 5: 60,150
Standard sample 6: 27,600
Standard sample 7: 10,290
Standard sample 8: 5,000
Standard sample 9: 2,810
Standard sample 10: 850

The RI detection intensity was measured with respect to the elution time of the methacrylic resin or methacrylic resin composition under the conditions set forth above.

The weight average molecular weight (Mw) and the number average molecular weight (Mn) of the methacrylic resins and methacrylic resin compositions were determined based on calibration curves obtained through measurement of the calibration curve standard samples, and then Mw/Mn was calculated using the determined values.

(3. Vicat Softening Temperature)

The Vicat softening temperature (° C.) of methacrylic resin compositions obtained in the following examples and comparative examples was measured in accordance with ISO 306 under the following conditions.

Specimen shape: Length 80 mm, width 10 mm, thickness 4 mm
Conditioning: One week left at 23° C. and 50% RH
Load: 1 N
Heating rate: 50° C./hr The Vicat softening temperature (° C.) was taken to be the temperature at which a needle-shaped indenter of 1 mm in diameter penetrated to a depth of 1 mm.

(4. Stereoregularity)

With respect to each methacrylic resin and methacrylic resin composition obtained in the following production examples, examples, and comparative examples, 30 mg of the methacrylic resin or methacrylic resin composition was dissolved in 0.6 mL of deuterated chloroform and was measured using the following $^1$H-NMR spectrometer and conditions.

Measurement device: AVANCE III 500HD Prodigy (produced by Bruker BioSpin)
Observation frequency: 500 MHz ($^1$H)
Integration count: 128 times
Measurement temperature: 23° C.
Internal standard substance: Tetramethylsilane The obtained results were used to draw a base line in a chemical shift (δ) range of 0 ppm to 3 ppm, and then integrated values were determined in a range of 0.65 ppm to 0.90 ppm for a syndiotactic chain fraction (rr), in a range of 0.98 ppm to 1.07 ppm for a heterotactic chain fraction (mr), and in a range of 1.16 ppm to 1.25 ppm for an isotactic chain fraction (mm).

In each case, the ratio (S/H) of the integrated intensity (S) of the syndiotactic fraction (rr) relative to the integrated intensity (H) of the heterotactic fraction (mr) was calculated as an indicator of stereoregularity.

<5. Proportion of Methanol-Soluble Content>

With respect to each methacrylic resin composition obtained in the following examples and comparative examples, 5 g of the methacrylic resin composition was dissolved in 100 mL of chloroform. The resultant solution was added into a dropping funnel and was then dripped into approximately 1 L of methanol stirred by a stirrer over 1 hour to cause re-precipitation. After the entire solution had been dripped into the methanol and then been left for 1 hour at rest, vacuum filtration was performed using a membrane filter (T05A090C produced by Advantec Mfs. Inc.) as a filter.

The filtration residue was vacuum dried for 16 hours at 60° C. and the dried product was taken to be methanol-insoluble content. Additionally, solvent was removed from the filtrate using a rotary evaporator with a bath temperature of 40° C. and a degree of vacuum that was gradually reduced from an initial setting of 390 Torr to a final level of 30 Torr. Soluble content remaining in the rotary evaporator flask was collected and taken to be methanol-soluble content.

The mass of the methanol-insoluble content and the mass of the methanol-soluble content were weighed and then the amount of the methanol-soluble content was calculated as a proportion (mass %; proportion of methanol-soluble content) relative to the total amount (100 mass %) of the methanol-soluble content and the methanol-insoluble content.

<6. Photoelastic Coefficient ($C_R$)>

Each of the methacrylic resin compositions obtained in the examples and comparative examples was formed into a pressed film using a vacuum compression molding machine to obtain a measurement sample.

Specifically, the sample was prepared by using a vacuum compression molding machine (SFV-30 produced by Shinto Metal Industries Corporation) to pre-heat the resin composition for 10 minutes at 260° C. under vacuum (approximately 10 kPa) and subsequently compress the resin composition for 5 minutes at 260° C. and approximately 10 MPa, and by then releasing the vacuum and press pressure and transferring the resin composition to a compression molding machine for cooling in which the resin composition was cooled and solidified. The resultant pressed film was cured for at least 24 hours in a constant temperature and constant humidity chamber adjusted to a temperature of 23° C. and a humidity of 60%, and then a measurement specimen (thickness: approximately 150 μm, width: 6 mm) was cut out therefrom.

The photoelastic coefficient $C_R$ (Pa$^{-1}$) was measured using a birefringence measurement device that is described in detail in Polymer Engineering and Science 1999, 39, 2349-2357.

The film-shaped specimen was set in a film tensing device (produced by Imoto Machinery Co., Ltd.) set up in the same constant temperature and constant humidity chamber such that the chuck separation was 50 mm. Next, a birefringence measurement device (RETS-100 produced by Ostuka Electronics Co., Ltd.) was set up such that a laser light path of the device was positioned in a central portion of the film. The birefringence of the specimen was measured while applying tensile stress with a strain rate of 50%/min (chuck separation: 50 mm, chuck movement speed: 5 mm/min).

The photoelastic coefficient ($C_R$) (Pa$^{-1}$) was calculated by making a least squares approximation of the relationship between the absolute value (|Δn|) of the measured birefringence and the tensile stress ($\sigma_R$) and then determining the gradient of the resultant straight line. This calculation was performed using data in a tensile stress range of 2.5 MPa≤$\sigma_R$≤10 MPa.

$$C_R = |\Delta n|/\sigma_R$$

Note that the absolute value (|Δn|) of birefringence is a value shown below.

$$|\Delta n| = |nx - ny|$$

(nx: refractive index of tension direction; ny: refractive index of in-plane direction perpendicular to tension direction)

<7. Surface Shaping Properties>

(Production of Stretched Film)

A film was produced from each methacrylic resin composition obtained in the following examples and comparative examples using a 50 mm φ single-screw extruder equipped with a filter for resin filtration (leaf filter produced by Nagase & Co., Ltd.) and a T-die of 480 mm in width at the tip of the extruder.

In production, an unstretched film of 250 μm in thickness was obtained with film production conditions of an extruder temperature setting of 260° C., a T-die temperature setting of 255° C., a discharge rate of 8 kg/hr, and a cooling roll temperature setting of the Vicat softening temperature –10° C.

This was followed by longitudinal stretching of the unstretched film using a roll stretching device including, in this order, a pair of pre-heating rolls, a pair of stretching rolls, an infrared heater disposed between the stretching rolls, and a pair of conveying rolls.

The temperature of each of the rolls was set as follows using the Vicat softening temperature of the resin composition being evaluated as a reference.

Pre-heating roll temperature: Vicat softening temperature+10° C.
Low-speed stretching roll temperature: Vicat softening temperature+30° C.
High-speed stretching roll temperature: Vicat softening temperature+10° C.
Conveying roll temperature: Vicat softening temperature –10° C.

The distance between the low-speed stretching roll and the high-speed stretching roll was 200 mm. The circumferential speed difference of the high/low-speed stretching rolls under these temperature conditions was set as 2.5 times.

The longitudinal stretching described above was followed by transverse stretching of the longitudinally stretched film using a tenter-type transverse stretching device including, in order from a film inlet side thereof, a pre-heating section, a transverse stretching section, and a heat treatment section. The temperatures of the sections inside the tenter-type device were set as follows using the Vicat softening temperature of the resin composition being evaluated as a reference.

Pre-heating section: Vicat softening temperature (° C.)
Transverse stretching section: Vicat softening temperature+10° C.
Heat treatment section: Vicat softening temperature (° C.)

After transverse stretching by 2.5 times had been performed under these conditions, the stretched film was released from the clips and was supplied into a trimming device equipped with a shear cutter. Both edge sections of the film were severed to obtain a biaxially stretched film having an average thickness of 40 μm. A rolled product was then obtained by winding 1000 m in length of the obtained film around a core made of 6 inch ABS.

(Knurling Conditions 1)

The obtained biaxially stretched film was subjected to knurling under the following conditions.

The knurling was performed using an apparatus including a pre-heating roll for pre-heating the film prior to knurling, and also including a knurling roll and a support roll for nipping the film to perform knurling thereon. The knurling was performed under the following conditions using an emboss roll.

Conveyance (line) speed: 40 m/min
Pre-heating roll temperature: 100° C.
Knurling roll temperature: Vicat softening temperature+30° C. (made of metal; induction heating roll used)
Support roll temperature: 60° C. (made of metal; induction heating roll used)
Knurling position: 15 mm to 25 mm from film edge
Knurled surface: One surface only
Knurling width: 10 mm
Knurling height: 15 μm
Nip linear pressure: 20 kgf/cm
Protrusion/recess density: Approximately 100 per $cm^2$
Protrusion/recess shape: Diamond shape The following methods were used to evaluate knurling thickness, shape replicability, and processability with respect to the film obtained after knurling.

(Knurling Thickness)

A thickness meter produced by Mitutoyo Corporation was used to measure the difference between the vertex of a protrusion of the knurling pattern and a section of the film that had not been subjected to knurling. Measurements were made at 3 points in the width direction of the section subjected to knurling and then, with respect to the point yielding the largest value, measurements were made at 10 points at 1 cm intervals in the length direction, and the average value for these points was taken to be the knurling thickness (μm).

(Shape Replicability)

The number of protrusions was measured using a microscope produced by Keyence Corporation. Shape replicability was then evaluated by the following standard.
Excellent: At least 80 protrusions per $cm^2$
Good: 50 to 80 protrusions per $cm^2$
Poor: Fewer than 50 protrusions per $cm^2$ (Processability)

Processability was evaluated based on the occurrence or absence of continuous processing malfunction and cracking that are associated with fusion or adhesion to a knurled section of film during knurling. The occurrence or absence of cracking was confirmed by inspecting the processed film by eye.
Excellent: Continuous processing is possible and cracking does not occur
Good: Continuous processability is poor or cracking is observed Poor: Continuous processability is poor and cracking is observed (Knurling Conditions 2: Alteration of Conveyance Speed)

Evaluation was performed in the same way as under knurling conditions 1 with the exception that the conveyance (line) speed of the film subjected to knurling was changed to 60 m/min.

(Knurling Conditions 3: Alteration of Temperature)

Evaluation was performed in the same way as under knurling conditions 1 with the exception that the knurling roll temperature during knurling was changed to the Vicat softening temperature+60° C.

(Storage Stability)

The rolled product obtained under knurling conditions 1 set forth above was stored for 2 weeks under conditions of a temperature of 40° C. and humidity of 80% RH. Thereafter, 100 m of film was unrolled from the rolled product, and film-on-film sticking was inspected to make a three-grade classification based on the sticking state.
Excellent: No sticking
Good: Slight sticking but easily peelable
Poor: Strong sticking and not easily peelable

[Raw Materials]

Raw materials used in the following examples and comparative examples were as shown below.

(Monomers)
Methyl methacrylate (produced by Asahi Kasei Chemicals Corporation)
N-Phenylmaleimide (phMI) (produced by Nippon Shokubai Co., Ltd.)
N-Cyclohexylmaleimide (chMI) (produced by Nippon Shokubai Co., Ltd.)
Methyl 2-(hydroxymethyl)acrylate (MHMA) (produced by Combi-Blocks Inc.)

(Antioxidants)
Irganox 1010 (produced by BASF)
ADK STAB PEP36 (produced by Adeka Corporation)

Production Example 1-1

A mixed monomer solution was prepared by measuring out 146.0 kg of methyl methacrylate (hereinafter, denoted as "MMA"), 4.0 kg of N-phenylmaleimide (hereinafter, denoted as "phMI"), 32.5 kg of N-cyclohexylmaleimide (hereinafter, denoted as "chMI"), 0.21 kg of n-octyl mercaptan as a chain transfer agent, and 147.0 kg of methyl isobutyl ketone (hereinafter, denoted as "MIBK"), adding these materials into a 1.25 $m^3$ reactor equipped with a stirring blade and a temperature controller functioning through use of a jacket, and then stirring these materials.

Next, a mixed monomer solution for subsequent addition was prepared by measuring out 260.4 kg of MMA, 7.5 kg of phMI, 71.3 kg of chMI, and 273.0 kg of MIBK, adding these materials into a first tank, and then stirring these materials. In addition, 58.0 kg of MMA was measured out in a second tank.

The reactor, the first tank, and the second tank were each subjected to 30 minutes of nitrogen bubbling at a rate of 10 L/min to remove dissolved oxygen.

Thereafter, the internal temperature of the reactor was raised to 100° C. while performing stirring at 50 rpm, and then a polymerization initiator solution containing 0.54 kg of 1,1-di(t-butylperoxy)cyclohexane dissolved in 4.46 kg of MIBK was added as in (1) to (5) of the following addition profile to perform polymerization.
(1) 0.0 hr to 0.5 hr: Feed rate of 2.0 kg/hr
(2) 0.5 hr to 3.5 hr: Feed rate of 1.0 kg/hr
(3) 3.5 hr to 4.5 hr: Feed rate of 0.5 kg/hr
(4) 4.5 hr to 6.0 hr: Feed rate of 0.25 kg/hr
(5) 6.0 hr to 7.0 hr: Feed rate of 0.125 kg/hr The solution temperature inside the reactor during polymerization was controlled to 110±2° C. through temperature adjustment using the jacket. Once 30 minutes had passed from the start of polymerization, the mixed monomer solution for subsequent addition was added from the first tank at an addition rate of 306 kg/hr.

Next, once 3 hours had passed from the start of polymerization, the entire amount of MMA in the second tank was added over 30 minutes at an addition rate of 116 kg/hr.

After addition of the polymerization initiator solution was completed, the polymerization reaction was continued for a further 3 hours to yield a polymerization solution containing a methacrylic resin having a cyclic structure-containing main chain.

Irganox 1010 was added to the polymerization solution under stirring in an amount of 0.1 parts by mass per 100 parts by mass of polymer contained in the solution.

Thereafter, the polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m$^2$ and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a composition (1-1) containing a methacrylic resin polymerized product having a cyclic structure-containing main chain.

It was confirmed that the chemical composition of the obtained composition (1-1) comprised structural units derived from the monomers MMA, phMI, and chMI in proportions of 80.3 mass %, 1.9 mass %, and 17.8 mass %, respectively. Moreover, the weight average molecular weight (Mw) was 246,000 and the S/H ratio used as an indicator of stereoregularity was 1.42.

Production Example 1-2

A mixed monomer solution was prepared by measuring out 146.0 kg of MMA, 28.5 kg of phMI, 8.0 kg of chMI, 0.85 kg of n-octyl mercaptan as a chain transfer agent, and 147.0 kg of toluene (hereinafter, denoted as "ToL"), adding these materials into a 1.25 m$^3$ reactor equipped with a stirring blade and a temperature controller functioning through use of a jacket, and then stirring these materials.

Next, a mixed monomer solution for subsequent addition was prepared by measuring out 271.4 kg of MMA, 52.9 kg of phMI, 14.9 kg of chMI, and 273.0 kg of ToL, adding these materials into a first tank, and then stirring these materials. In addition, 58.0 kg of MMA was measured out in a second tank.

The reactor, the first tank, and the second tank were each subjected to 30 minutes of nitrogen bubbling at a rate of 10 L/min to remove dissolved oxygen.

Thereafter, the internal temperature of the reactor was raised to 95° C. while performing stirring at 50 rpm, and then a polymerization initiator solution containing 0.35 kg of t-butylperoxy isopropyl monocarbonate dissolved in 4.65 kg of ToL was added as in (1) to (5) of the following addition profile to perform polymerization.
(1) 0.0 hr to 0.5 hr: Feed rate of 2.0 kg/hr
(2) 0.5 hr to 3.5 hr: Feed rate of 1.0 kg/hr
(3) 3.5 hr to 4.5 hr: Feed rate of 0.5 kg/hr
(4) 4.5 hr to 6.0 hr: Feed rate of 0.25 kg/hr
(5) 6.0 hr to 7.0 hr: Feed rate of 0.125 kg/hr The solution temperature inside the reactor during polymerization was controlled to 110±2° C. through temperature adjustment using the jacket.

Once 30 minutes had passed from the start of polymerization, the mixed monomer solution for subsequent addition was added from the first tank at an addition rate of 306 kg/hr.

Next, once 3 hours had passed from the start of polymerization, the entire amount of MMA in the second tank was added over 30 minutes at an addition rate of 116 kg/hr.

After addition of the polymerization initiator solution was completed, the polymerization reaction was continued for a further 3 hours to yield a polymerization solution containing a methacrylic resin having a cyclic structure-containing main chain.

Irganox 1010 was added to the polymerization solution under stirring in an amount of 0.1 parts by mass per 100 parts by mass of polymer contained in the solution.

Thereafter, the polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m$^2$ and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a composition (1-2) containing a methacrylic resin polymerized product having a cyclic structure-containing main chain.

It was confirmed that the chemical composition of the obtained pelletized composition (1-2) comprised structural units derived from the monomers MMA, phMI, and chMI in proportions of 82.0 mass %, 14.1 mass %, and 3.9 mass %, respectively. Moreover, the weight average molecular weight (Mw) was 102,000 and the S/H ratio used as an indicator of stereoregularity was 1.26.

Production Example 1-3

A mixed monomer solution was prepared by measuring out 146.0 kg of MMA, 4.6 kg of phMI, 32.0 kg of chMI, 0.21 kg of n-octyl mercaptan as a chain transfer agent, and 147.0 kg of ToL, adding these materials into a 1.25 m$^3$ reactor equipped with a stirring blade and a temperature controller functioning through use of a jacket, and then stirring these materials.

Next, a mixed monomer solution (1) for subsequent addition was prepared by measuring out 271.2 kg of MMA, 37.1 kg of phMI, 30.9 kg of chMI, and 265.0 kg of ToL, adding these materials into a first tank, and then stirring these materials. In addition, 58.0 kg of MMA was prepared in a second tank.

The reactor, the first tank, and the second tank were each subjected to 30 minutes of nitrogen bubbling at a rate of 10 L/min to remove dissolved oxygen.

Thereafter, the internal temperature of the reactor was raised to 100° C. while performing stirring at 50 rpm, and then a polymerization initiator solution containing 0.35 kg of t-butylperoxy isopropyl monocarbonate dissolved in 4.65 kg of ToL was added as in (1) to (5) of the following addition profile to perform polymerization.

(1) 0.0 hr to 0.5 hr: Feed rate of 2.0 kg/hr
(2) 0.5 hr to 3.5 hr: Feed rate of 1.0 kg/hr
(3) 3.5 hr to 4.5 hr: Feed rate of 0.5 kg/hr
(4) 4.5 hr to 6.0 hr: Feed rate of 0.25 kg/hr
(5) 6.0 hr to 7.0 hr: Feed rate of 0.125 kg/hr The solution temperature inside the reactor during polymerization was controlled to 110±2° C. through temperature adjustment using the jacket.

Once 30 minutes has passed from the start of polymerization, the mixed monomer solution (1) for subsequent addition was added from the first tank at an addition rate of 306 kg/hr.

Next, once 2 hours had passed from the start of polymerization, the entire amount of MMA in the second tank was added over 30 minutes at an addition rate of 116 kg/hr.

After addition of the polymerization initiator solution was completed, the polymerization reaction was continued for a further 3 hours to yield a polymerization solution containing a methacrylic resin having a cyclic structure-containing main chain.

Irganox 1010 was added to the polymerization solution under stirring in an amount of 0.1 parts by mass per 100 parts by mass of polymer contained in the solution.

Thereafter, the polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m$^2$ and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a methacrylic resin polymerized product (1-3) having a cyclic structure-containing main chain.

It was confirmed that the chemical composition of the obtained pelletized polymerized product (1-3) comprised structural units derived from the monomers MMA, phMI, and chMI in proportions of 81.1 mass %, 8.1 mass %, and 10.8 mass %, respectively. Moreover, the weight average molecular weight (Mw) was 142,000 and the S/H ratio used as an indicator of stereoregularity was 1.24.

Production Example 1-4

A mixed monomer solution was prepared by measuring out 163.0 kg of MMA, 8.1 kg of phMI, 11.6 kg of chMI, 0.85 kg of n-octyl mercaptan as a chain transfer agent, and 147.0 kg of ToL, adding these materials into a 1.25 m$^3$ reactor equipped with a stirring blade and a temperature controller functioning through use of a jacket, and then stirring these materials.

Next, a mixed monomer solution for subsequent addition was prepared by measuring out 302.6 kg of MMA, 15.1 kg of phMI, 21.5 kg of chMI, and 273.0 kg of ToL, adding these materials into a first tank, and then stirring these materials. In addition, 58.0 kg of MMA was measured out in a second tank.

The reactor, the first tank, and the second tank were each subjected to 30 minutes of nitrogen bubbling at a rate of 10 L/min to remove dissolved oxygen.

Thereafter, the internal temperature of the reactor was raised to 100° C. while performing stirring at 50 rpm, and then a polymerization initiator solution containing 0.54 kg of 1,1-di(t-butylperoxy)cyclohexane dissolved in 4.46 kg of ToL was added as in (1) to (5) of the following addition profile to perform polymerization.

(1) 0.0 hr to 0.5 hr: Feed rate of 2.0 kg/hr
(2) 0.5 hr to 3.5 hr: Feed rate of 1.0 kg/hr
(3) 3.5 hr to 4.5 hr: Feed rate of 0.5 kg/hr
(4) 4.5 hr to 6.0 hr: Feed rate of 0.25 kg/hr
(5) 6.0 hr to 7.0 hr: Feed rate of 0.125 kg/hr The solution temperature inside the reactor during polymerization was controlled to 110±2° C. through temperature adjustment using the jacket.

Once 30 minutes has passed from the start of polymerization, the mixed monomer solution for subsequent addition was added from the first tank at an addition rate of 306 kg/hr.

Next, once 3 hours had passed from the start of polymerization, the entire amount of MMA in the second tank was added over 30 minutes at an addition rate of 116 kg/hr.

After addition of the polymerization initiator solution was completed, the polymerization reaction was continued for a further 3 hours to yield a polymerization solution containing a methacrylic resin having a cyclic structure-containing main chain.

Irganox 1010 was added to the polymerization solution under stirring in an amount of 0.1 parts by mass per 100 parts by mass of polymer contained in the solution.

Thereafter, the polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m$^2$ and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a composition (1-4) containing a methacrylic resin polymerized product having a cyclic structure-containing main chain.

It was confirmed that the chemical composition of the obtained composition (1-4) comprised structural units derived from the monomers MMA, phMI, and chMI in proportions of 90.3 mass %, 4.0 mass %, and 5.7 mass %, respectively. Moreover, the weight average molecular weight (Mw) was 95,000 and the S/H ratio used as an indicator of stereoregularity was 1.35.

Production Example 1-5

A mixed monomer solution was prepared by measuring out 108.1 kg of MMA, 32.1 kg of phMI, 42.4 kg of chMI, 0.78 kg of n-octyl mercaptan as a chain transfer agent, and 147.0 kg of ToL, adding these materials into a 1.25 m³ reactor equipped with a stirring blade and a temperature controller functioning through use of a jacket, and then stirring these materials Next, a mixed monomer solution for subsequent addition was prepared by measuring out 201 kg of MMA, 59.5 kg of phMI, 78.8 kg of chMI, and 273.0 kg of ToL, adding these materials into a first tank, and then stirring these materials. In addition, 58.0 kg of MMA was measured out in a second tank.

The reactor, the first tank, and the second tank were each subjected to 30 minutes of nitrogen bubbling at a rate of 10 L/min to remove dissolved oxygen.

Thereafter, the internal temperature of the reactor was raised to 100° C. while performing stirring at 50 rpm, and then a polymerization initiator solution containing 0.54 kg of 1,1-di(t-butylperoxy)cyclohexane dissolved in 4.46 kg of ToL was added as in (1) to (5) of the following addition profile to perform polymerization.

(1) 0.0 hr to 0.5 hr: Feed rate of 2.0 kg/hr
(2) 0.5 hr to 3.5 hr: Feed rate of 1.0 kg/hr
(3) 3.5 hr to 4.5 hr: Feed rate of 0.5 kg/hr
(4) 4.5 hr to 6.0 hr: Feed rate of 0.25 kg/hr
(5) 6.0 hr to 7.0 hr: Feed rate of 0.125 kg/hr The solution temperature inside the reactor during polymerization was controlled to 110±2° C. through temperature adjustment using the jacket.

Once 30 minutes has passed from the start of polymerization, the mixed monomer solution for subsequent addition was added from the first tank at an addition rate of 306 kg/hr.

Next, once 3 hours had passed from the start of polymerization, the entire amount of MMA in the second tank was added over 30 minutes at an addition rate of 116 kg/hr.

After addition of the polymerization initiator solution was completed, the polymerization reaction was continued for a further 3 hours to yield a polymerization solution containing a methacrylic resin having a cyclic structure-containing main chain.

Irganox 1010 was added to the polymerization solution under stirring in an amount of 0.1 parts by mass per 100 parts by mass of polymer contained in the solution.

Thereafter, the polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m² and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a methacrylic resin composition (1-5) having a cyclic structure-containing main chain.

It was confirmed that the chemical composition of the obtained composition (1-5) comprised structural units derived from the monomers MMA, phMI, and chMI in proportions of 63.3 mass %, 15.8 mass %, and 20.9 mass %, respectively. Moreover, the weight average molecular weight (Mw) was 99,000 and the S/H ratio used as an indicator of stereoregularity was 1.15.

Production Example 1-6

A mixed monomer solution was prepared by measuring out 146.0 kg of MMA, 28.5 kg of phMI, 8.0 kg of chMI, 0.15 kg of n-octyl mercaptan as a chain transfer agent, and 147.0 kg of MIBK, adding these materials into a 1.25 m³ reactor equipped with a stirring blade and a temperature controller functioning through use of a jacket, and then stirring these materials.

Next, a mixed monomer solution for subsequent addition was prepared by measuring out 271.4 kg of MMA, 52.9 kg of phMI, 14.9 kg of chMI, and 273.0 kg of MIBK, adding these materials into a first tank, and then stirring these materials. In addition, 58.0 kg of MMA was measured out in a second tank.

The reactor, the first tank, and the second tank were each subjected to 30 minutes of nitrogen bubbling at a rate of 10 L/min to remove dissolved oxygen.

Thereafter, the internal temperature of the reactor was raised to 95° C. while performing stirring at 50 rpm, and then a polymerization initiator solution containing 0.35 kg of t-butylperoxy isopropyl monocarbonate dissolved in 4.65 kg of MIBK was added as in (1) to (5) of the following addition profile to perform polymerization.

(1) 0.0 hr to 0.5 hr: Feed rate of 2.0 kg/hr
(2) 0.5 hr to 3.5 hr: Feed rate of 1.0 kg/hr
(3) 3.5 hr to 4.5 hr: Feed rate of 0.5 kg/hr
(4) 4.5 hr to 6.0 hr: Feed rate of 0.25 kg/hr
(5) 6.0 hr to 7.0 hr: Feed rate of 0.125 kg/hr The solution temperature inside the reactor during polymerization was controlled to 110±2° C. through temperature adjustment using the jacket.

Once 30 minutes had passed from the start of polymerization, the mixed monomer solution for subsequent addition was added from the first tank at an addition rate of 306 kg/hr.

Next, once 3 hours had passed from the start of polymerization, the entire amount of MMA in the second tank was added over 30 minutes at an addition rate of 116 kg/hr.

Thereafter, the polymerization reaction was continued for a further 3 hours to obtain a polymerization solution containing a methacrylic resin having a cyclic structure-containing main chain.

Irganox 1010 was added to the polymerization solution under stirring in an amount of 0.1 parts by mass per 100 parts by mass of polymer contained in the solution.

Thereafter, the polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m² and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a composition (1-6) containing a methacrylic resin polymerized product having a cyclic structure-containing main chain.

It was confirmed that the chemical composition of the obtained pelletized composition (1-6) comprised structural units derived from the monomers MMA, phMI, and chMI in proportions of 82.0 mass %, 14.1 mass %, and 3.9 mass %, respectively. Moreover, the weight average molecular weight (Mw) was 226,000 and the S/H ratio used as an indicator of stereoregularity was 1.26.

Production Example 2

A mixed monomer solution was prepared by measuring out 146.0 kg of MMA, 14.6 kg of phMI, 22.0 kg of chMI, 0.17 kg of n-octyl mercaptan as a chain transfer agent, and 147.0 kg of m-xylene (hereinafter, denoted as "mXy"), adding these materials into a 1.25 m$^3$ reactor equipped with a stirring blade and a temperature controller functioning through use of a jacket, and then stirring these materials.

Next, a mixed monomer solution for subsequent addition was prepared by measuring out 271.2 kg of MMA, 27.1 kg of phMI, 40.9 kg of chMI, and 273.0 kg of mXy, adding these materials into a first tank, and then stirring these materials. In addition, 58.0 kg of MMA was measured out in a second tank.

The reactor, the first tank, and the second tank were each subjected to 30 minutes of nitrogen bubbling at a rate of 10 L/min to remove dissolved oxygen.

Thereafter, the solution temperature in the reactor was raised to 100° C. by blowing steam into the jacket, and then the contents of the reactor were stirred at 50 rpm while adding a polymerization initiator solution containing 0.35 kg of t-butylperoxy isopropyl monocarbonate dissolved in 4.65 kg of mXy at a rate of 2 kg/hr to initiate polymerization.

The solution temperature inside the reactor during polymerization was controlled to 110±2° C. through temperature adjustment using the jacket.

Once 30 minutes had passed from the start of polymerization, the addition rate of the initiator solution was reduced to 1 kg/hr and the mixed monomer solution for subsequent addition was added from the first tank over 2 hours at 306.2 kg/hr. Next, once 2 hours and 45 minutes had passed from the start of polymerization, the entire amount of MMA in the second tank was added over 30 minutes at a rate of 116 kg/hr.

Moreover, the addition rate of the initiator solution was reduced to 0.5 kg/hr once 3.5 hours had passed from the start of polymerization, 0.25 kg/hr once 4.5 hours had passed from the start of polymerization, and 0.125 kg/hr once 6 hours had passed from the start of polymerization, and addition was stopped once 7 hours had passed from the start of polymerization.

A polymerization solution containing a methacrylic resin having a cyclic structure-containing main chain was obtained once 10 hours had passed from the start of polymerization.

Irganox 1010 was added to the polymerization solution under stirring in an amount of 0.1 parts by mass per 100 parts by mass of polymer contained in the solution.

The resultant polymerization solution was fed into a concentrating device comprising a tubular heat exchanger and a vaporization tank that had been pre-heated to 170° C., and the concentration of polymer contained in the solution was raised to 70 mass %.

The resultant polymerization solution was fed into a thin film evaporator having a heat transfer area of 0.2 m$^2$ and was subjected to devolatilization. The devolatilization was carried out with an evaporator internal temperature of 280° C., a feed rate of 30 L/hr, a rotational speed of 400 rpm, and a degree of vacuum of 30 Torr. The polymerized product subjected to devolatilization was then pressurized using a gear pump, extruded from a strand die, cooled by water, and subsequently pelletized to obtain a composition (2) containing a methacrylic resin polymerized product having a cyclic structure-containing main chain.

It was confirmed that the chemical composition of the obtained pelletized composition (2) comprised structural units derived from the monomers MMA, phMI, and chMI in proportions of 81.3 mass %, 7.9 mass %, and 10.8 mass %, respectively. Moreover, the weight average molecular weight (Mw) was 157,000 and the S/H ratio used as an indicator of stereoregularity was 1.25.

Production Example 3

A mixed monomer solution was prepared by measuring out 450.7 kg of MMA, 39.8 kg of phMI, 59.7 kg of chMI, 0.41 kg of n-octyl mercaptan as a chain transfer agent, and 450 kg of mXy, adding these materials into a 1.25 m$^3$ reactor that had been purged with nitrogen in advance, and then stirring these materials.

Next, the mixed monomer solution was subjected to 6 hours of nitrogen bubbling at a rate of 100 mL/min to remove dissolved oxygen, and then the temperature of the mixed monomer solution was raised to 110° C.

A polymerization initiator solution containing 0.30 kg of t-butylperoxy isopropyl monocarbonate as a polymerization initiator dissolved in 3.85 kg of mXy was subsequently added at a rate of 1 kg/hr to perform polymerization.

A polymerization solution containing a methacrylic resin having a cyclic structure-containing main chain was obtained once 10 hours had passed from the start of polymerization.

Irganox 1010 was added to the polymerization solution under stirring in an amount of 0.1 parts by mass per 100 parts by mass of polymer contained in the solution.

The polymerization solution was then subjected to concentration, devolatilization, and pelletization in the same way as in Production Example 1-1 to obtain a pelletized composition (3) containing a methacrylic resin polymerized product including N-substituted maleimide structural units.

It was confirmed that the chemical composition of the obtained composition (3) comprised structural units derived from the monomers MMA, phMI, and chMI in proportions of 81.3 mass %, 7.9 mass %, and 10.8 mass %, respectively. Moreover, the weight average molecular weight (Mw) was 155,000 and the S/H ratio used as an indicator of stereoregularity was 1.25.

Production Example 4-1

A raw material solution was prepared by charging 149.6 kg of MMA, 37.4 kg of methyl 2-(hydroxymethyl)acrylate, 0.04 kg of tris(2,4-di-t-butylphenyl) phosphite, 149.0 kg of MIBK, and 25 g of n-dodecyl mercaptan into a 1 m$^3$ reactor that was equipped with a stirrer, a temperature sensor, a cooling tube, and a nitrogen gas supply tube, and that had been internally purged with nitrogen in advance. The reactor was stirred and the internal temperature of the reactor was raised to 100° C. while passing nitrogen therethrough.

A polymerization initiator solution was separately prepared by mixing 0.56 kg of t-amyl peroxyisononanoate as a polymerization initiator and 3.6 kg of MIBK.

Once the temperature of the raw material solution reached 100° C., the initiator solution was added as in (1) to (6) of the following addition profile to initiate polymerization.

(1) 0.0 hr to 0.5 hr: Feed rate of 2.0 kg/hr
(2) 0.5 hr to 1.0 hr: Feed rate of 1.0 kg/hr (3) 1.0 hr to 2.0 hr: Feed rate of 0.8 kg/hr (4) 2.0 hr to 3.0 hr: Feed rate of 0.7 kg/hr (5) 3.0 hr to 4.0 hr: Feed rate of 0.35 kg/hr (6) 4.0 hr to 7.0 hr: Feed rate of 0.27 kg/hr After addition of the initiator had been completed, the reaction was continued for a further 2 hours to complete the polymerization reaction.

The internal temperature during the polymerization reaction was controlled to 105° C. to 110° C.

Next, 85 kg of MIBK and 170 g of a mixture of the organophosphorus compounds stearyl phosphate and distearyl phosphate as a cyclization catalyst were added to the resultant polymer solution, and a cyclocondensation reaction was carried out for 2 hours under reflux at approximately 95° C. to 100° C.

The resultant polymer solution was subsequently heated to 240° C. in a heater comprising a multi-tube heat exchanger and was then introduced into a vented twin-screw extruder equipped with one rear vent and four front vents so as to continue the cyclization reaction while performing devolatilization.

The conditions in the twin-screw extruder were a feed rate of the resultant copolymer solution of 15 kg/hr in terms of resin, a barrel temperature of 260° C., a rotational speed of 100 rpm, and a degree of vacuum of 10 Torr to 300 Torr. During the above, a catalyst deactivator (zinc 2-ethylhexanoate; produced by Nihon Kagaku Sangyo Co., Ltd.; product name: NIKKA OCTHIX Zn 18%) and Irganox 1010 were fed from two side feeds provided in a downstream half of the twin-screw extruder. The deactivator and Irganox 1010 were added with respective feed rates of 30 g/hr and 15 g/hr, as toluene solutions, for the same time as the feed time of the resin.

The cyclized polymerized product subjected to cyclization and devolatilization treatment by the twin-screw extruder was extruded from a strand die, cooled by water, and then pelletized to obtain a composition (4-1) containing a methacrylic resin polymerized product.

It was confirmed that the chemical composition of the obtained composition (4-1) comprised lactone ring structural units in a proportion of 28.3 mass %. The content of lactone ring structural units was determined by a method described in JP 2007-297620 A. The obtained composition (4-1) had a weight average molecular weight (Mw) of 209,000 and an S/H ratio, used as an indicator of stereoregularity, of 1.40.

Production Example 4-2

A raw material solution was prepared by charging 136.6 kg of MMA, 37.4 kg of methyl 2-(hydroxymethyl)acrylate, 13.0 kg of styrene, 0.04 kg of tris(2,4-di-t-butylphenyl) phosphite, 149.0 kg of ToL, and 125 g of n-dodecyl mercaptan into a 1 m³ reactor that was equipped with a stirrer, a temperature sensor, a cooling tube, and nitrogen gas supply tube, and that had been internally purged with nitrogen in advance. The reactor was stirred and the internal temperature of the reactor was raised to 100° C. while passing nitrogen therethrough.

A solution for separate addition was separately prepared by mixing 0.56 kg of t-amyl peroxyisononanoate as a polymerization initiator and 6.5 kg of styrene.

Once the temperature of the raw material solution reached 100° C., the solution for separate addition was added as in (1) to (5) of the following addition profile to initiate polymerization.

(1) 0.0 hr to 0.5 hr: Feed rate of 5.0 kg/hr (2) 0.5 hr to 1.0 hr: Feed rate of 3.0 kg/hr (3) 1.0 hr to 3.0 hr: Feed rate of 1.0 kg/hr (4) 3.0 hr to 4.0 hr: Feed rate of 0.35 kg/hr (5) 4.0 hr to 7.0 hr: Feed rate of 0.27 kg/hr After addition of the polymerization initiator had been completed, the reaction was continued for a further 2 hours to complete the polymerization reaction.

The internal temperature during the polymerization reaction was controlled to 105° C. to 110° C.

Next, 85 kg of ToL and 170 g of a mixture of the organophosphorus compounds stearyl phosphate and distearyl phosphate as a cyclization catalyst were added to the resultant polymer solution, and a cyclocondensation reaction was carried out for 2 hours under reflux at approximately 95° C. to 100° C.

The resultant polymer solution was subsequently heated to 240° C. in a heater comprising a multi-tube heat exchanger and was then introduced into a vented twin-screw extruder equipped with one rear vent and four front vents so as to continue the cyclization reaction while performing devolatilization.

The conditions in the twin-screw extruder were a feed rate of the resultant copolymer solution of 15 kg/hr in terms of resin, a barrel temperature of 260° C., a rotational speed of 100 rpm, and a degree of vacuum of 10 Torr to 300 Torr.

During the above, a catalyst deactivator (zinc 2-ethylhexanoate; produced by Nihon Kagaku Sangyo Co., Ltd.; product name: NIKKA OCTHIX Zn 18%) and Irganox 1010 were fed from two side feeds provided in a downstream half of the twin-screw extruder. The deactivator and Irganox 1010 were added with respective feed rates of 30 g/hr and 15 g/hr, as toluene solutions, for the same time as the feed time of the resin.

The cyclized polymerized product subjected to cyclization and devolatilization treatment by the twin-screw extruder was extruded from a strand die, cooled by water, and then pelletized to obtain a composition (4-2) containing a methacrylic resin polymerized product.

It was confirmed that the chemical composition of the obtained composition (4-2) comprised lactone ring structural units in a proportion of 28.3 mass % and styrene monomer-derived structural units in a proportion of 6.8 mass %. The content of lactone ring structural units was determined by the method described in JP 2007-297620 A. The obtained composition (4-2) had a weight average molecular weight (Mw) of 109,000 and an S/H ratio, used as an indicator of stereoregularity, of 1.26.

Production Example 4-3

A composition (4-3) containing a methacrylic resin polymerized product was produced in the same way as in Production Example 4-2 with the exception that the method in Production Example 4-2 was changed to a method in which n-dodecyl mercaptan was not used and in which the initiator solution was added for 2 hours at an addition rate of 3.58 kg/hr.

It was confirmed that the chemical composition of the obtained composition (4-3) comprised lactone ring structural units in a proportion of 28.3 mass % and styrene monomer-derived structural units in a proportion of 6.5 mass %. The content of lactone ring structural units was determined by the method described in JP 2007-297620 A.

The obtained composition (4-3) had a weight average molecular weight (Mw) of 142,000 and an S/H ratio, used as an indicator of stereoregularity, of 1.28.

Production Example 5

A mixed liquid was prepared by charging 2 kg of water, 65 g of tricalcium phosphate, 39 g of calcium carbonate, and 0.39 g of sodium lauryl sulfate to a vessel having a stirrer equipped with four pitched-paddle blades, and then mixing these materials.

Next, 26 kg of water was charged to a 60 L reactor having a stirrer equipped with three retreated blades and was heated to 40° C. Thereafter, 18.6 kg of MMA, 1.8 kg of phMI, 2.5 kg of chMI, 0.04 kg of lauroyl peroxide as a polymerization initiator, 0.015 kg of n-octyl mercaptan as a chain transfer agent, and the previously prepared mixed liquid were added into the reactor and were mixed by stirring.

Next, heating was performed to 75° C. at a rate of approximately 1° C./min and suspension polymerization was carried out while maintaining the temperature at approximately 75° C. A heat generation peak was observed approximately 150 minutes after addition of the raw material mixture.

Thereafter, heating was performed to approximately 96° C. at a rate of approximately 1° C./min, and aging was performed for 120 minutes to substantially complete the polymerization reaction.

Next, cooling was performed to 50° C. and 20 mass % sulfuric acid was added for suspension agent dissolution.

The polymerization reaction solution was then passed through a sieve having a 1.68 mm mesh to remove aggregates, moisture was separated by filtration, and the resultant slurry was dehydrated to obtain a bead-shaped polymer. The bead-shaped polymer was washed with water and was then dehydrated in the same manner as above. The bead-shaped polymer was then washed through repeated washing with deionized water and dehydration to obtain a particulate methacrylic resin (5) having a cyclic structure-containing main chain.

It was confirmed that the chemical composition of the obtained polymerized product (5) comprised structural units derived from the monomers MMA, phMI, and chMI in proportions of 81.3 mass %, 7.9 mass %, and 10.8 mass %, respectively. The weight average molecular weight was 185,000, the Vicat softening temperature was 131° C., and the S/H ratio used as an indicator of stereoregularity was 1.95.

Example 1

The composition (1-1) obtained in Production Example 1-1 and the composition (1-2) obtained in Production Example 1-2 were vacuum dried for 5 hours at 90° C., cooled to 30° C. in a nitrogen atmosphere, and then used in preparation of a composition.

A tumbler-type mixer that had been purged with nitrogen in advance was used to prepare a mixture from 50 parts by mass of the composition (1-1), 50 parts by mass of the composition (1-2), and 0.1 parts by mass of ADK STAB PEP 36 as an antioxidant.

The resultant mixture was fed into and melt-kneaded by a 58 mm φ vented twin-screw extruder with use of dehumidified air adjusted to a dew point of −30° C. and a temperature of 80° C. A nitrogen supply line was provided in a lower part of a raw material hopper for the twin-screw extruder, and nitrogen was introduced into the extruder during the above operation. The oxygen concentration at the bottom of the raw material hopper was measured to be approximately 1 volume %.

Operation was performed under conditions of a temperature setting for a lower part of the extruder and a die of 270° C., a rotational speed of 200 rpm, a degree of vacuum in a vent part of 200 Torr, and a discharge rate of 20 kg/hr.

The melt-kneaded resin composition was extruded through a porous die as strands and was introduced into a cooling bath filled with cooling water that had been pre-heated to 50° C. The resin composition was cooled and solidified, and was cut using a cutter to obtain a pelletized composition.

It was confirmed that the chemical composition of the obtained pelletized composition (1) comprised structural units derived from the monomers MMA, phMI, and chMI in proportions of 81.2 mass %, 8.0 mass %, and 10.8 mass %, respectively.

The weight average molecular weight was 143,000, the Vicat softening temperature was 130° C., and the S/H ratio used as an indicator of stereoregularity was 1.34.

Other evaluation results are shown in Tables 1 and 2.

Example 2

A composition (2) was prepared in the same way as in Example 1 with the exception that the methacrylic resin compositions used in Example 1 were changed to 50 parts by mass of the composition (1-1) obtained in Production Example 1-1 and 50 parts by mass of the composition (1-4) obtained in Production Example 1-4.

It was confirmed that the chemical composition of the obtained pelletized composition (2) comprised structural units derived from the monomers MMA, phMI, and chMI in proportions of 85.2 mass %, 3.0 mass %, and 11.8 mass %, respectively.

The weight average molecular weight was 140,000, the Vicat softening temperature was 120° C., and the S/H ratio used as an indicator of stereoregularity was 1.39.

Other evaluation results are shown in Tables 1 and 2.

Example 3

A composition (3) was prepared in the same way as in Example 1 with the exception that the methacrylic resin compositions used in Example 1 were changed to 50 parts by mass of the composition (1-1) obtained in Production Example 1-1 and 50 parts by mass of the composition (1-5) obtained in Production Example 1-5.

It was confirmed that the chemical composition of the obtained pelletized composition (3) comprised structural units derived from the monomers MMA, phMI, and chMI in proportions of 71.8 mass %, 8.9 mass %, and 19.3 mass %, respectively.

The weight average molecular weight was 137,000, the Vicat softening temperature was 138° C., and the S/H ratio used as an indicator of stereoregularity was 1.29.

Other evaluation results are shown in Tables 1 and 2.

Example 4

A composition (4) was prepared in the same way as in Example 1 with the exception that the methacrylic resin compositions used in Example 1 were changed to 70 parts by mass of the composition (1-1) obtained in Production Example 1-1 and 30 parts by mass of the composition (1-2) obtained in Production Example 1-2.

It was confirmed that the chemical composition of the obtained pelletized composition (4) comprised structural units derived from the monomers MMA, phMI, and chMI in proportions of 81.5 mass %, 10.4 mass %, and 8.1 mass %, respectively.

The weight average molecular weight was 168,000, the Vicat softening temperature was 133° C., and the S/H ratio used as an indicator of stereoregularity was 1.37.

Other evaluation results are shown in Tables 1 and 2.

Example 5

A composition (5) was prepared in the same way as in Example 1 with the exception that the methacrylic resin compositions used in Example 1 were changed to 30 parts by mass of the composition (1-1) obtained in Production Example 1-1 and 70 parts by mass of the composition (1-2) obtained in Production Example 1-2.

It was confirmed that the chemical composition of the obtained pelletized composition (5) comprised structural units derived from the monomers MMA, phMI, and chMI in proportions of 80.8 mass %, 5.6 mass %, and 13.6 mass %, respectively.

The weight average molecular weight was 122,000, the Vicat softening temperature was 127° C., and the S/H ratio used as an indicator of stereoregularity was 1.31.

Other evaluation results are shown in Tables 1 and 2.

Example 6

A composition (6) was prepared in the same way as in Example 1 with the exception that the methacrylic resin compositions used in Example 1 were changed to 50 parts by mass of the composition (4-1) obtained in Production Example 4-1 and 50 parts by mass of the composition (4-2) obtained in Production Example 4-2.

It was confirmed that the chemical composition of the obtained pelletized composition (6) comprised lactone ring structural units in a proportion of 28.3 mass % and styrene monomer-derived structural units in a proportion of 3.4 mass %.

The weight average molecular weight was 148,000, the Vicat softening temperature was 124° C., and the S/H ratio used as an indicator of stereoregularity was 1.33.

Other evaluation results are shown in Tables 1 and 2.

Reference Example 7

A composition (7) was prepared in the same way as in Example 1 with the exception that the methacrylic resin compositions used in Example 1 were changed to 100 parts by mass of the polymerized product (1-3) obtained in Production Example 1-3.

It was confirmed that the chemical composition of the obtained pelletized composition (7) comprised structural units derived from the monomers MMA, phMI, and chMI in proportions of 81.3 mass %, 7.9 mass %, and 10.8 mass %, respectively.

The weight average molecular weight was 131,000, the Vicat softening temperature was 129° C., and the S/H ratio used as an indicator of stereoregularity was 1.24.

Other evaluation results are shown in Tables 1 and 2.

Example 8

A composition (8) was prepared in the same way as in Example 1 with the exception that the methacrylic resin compositions used in Example 1 were changed to 60 parts by mass of the composition (2) obtained in Production Example 2 and 40 parts by mass of the polymerized product (5) obtained in Production Example 5. It was confirmed that the chemical composition of the obtained pelletized composition (8) comprised structural units derived from the monomers MMA, phMI, and chMI in proportions of 81.3 mass %, 7.9 mass %, and 10.8 mass %, respectively.

The weight average molecular weight was 151,000, the Vicat softening temperature was 131° C., and the S/H ratio used as an indicator of stereoregularity was 1.49.

Other evaluation results are shown in Tables 1 and 2.

Reference Example 9

A composition (9) was prepared in the same way as in Example 1 with the exception that the methacrylic resin compositions used in Example 1 were changed to 50 parts by mass of the composition (1-1) obtained in Production Example 1-1 and 50 parts by mass of the composition (1-6) obtained in Production Example 1-6. It was confirmed that the chemical composition of the obtained pelletized composition (9) comprised structural units derived from the monomers MMA, phMI, and chMI in proportions of 81.3 mass %, 7.9 mass %, and 10.8 mass %, respectively.

The weight average molecular weight was 212,000, the Vicat softening temperature was 130° C., and the S/H ratio used as an indicator of stereoregularity was 1.34.

Other evaluation results are shown in Tables 1 and 2.

Example 10

An unstretched sheet of 1.5 mm in thickness was produced using the pelletized composition (4) obtained in Example 4. The unstretched sheet was produced using a 50 mm φ single-screw extruder having a gear pump and a T-die with a lip opening of 2.5 mm and a width of 480 mm positioned at the tip of the extruder, and with production conditions of an extruder temperature setting of 270° C., a T-die temperature setting of 265° C., and a discharge rate of 8 kg/hr.

The unstretched sheet was then longitudinally stretched with a stretching ratio of 2 times using a roll stretching device.

The roll temperature was set as the Vicat softening temperature+10° C.

The longitudinal stretching was followed by transverse stretching with a stretching ratio of 2 times using a tenter-type transverse stretching device with the stretching temperature set to the Vicat softening temperature+10° C. As a result, a sequentially biaxially stretched sheet of 35 μm in thickness was obtained. The photoelastic coefficient of the biaxially stretched sheet was $1.0 \times 10^{12}$ $Pa^{-1}$.

The obtained biaxially stretched sheet was subjected to surface shaping by press molding using the following mold.

<Mold Design>
Mold size: 30 mm square
Material: Nickel
Shaped pattern: Stripe
Pattern pitch: 1 μm
Pattern protrusion width: 0.5 μm
Pattern protrusion height: 1 μm <Shaping Conditions>
Mold temperature: 170° C.
Press pressure: 20 MPa
Holding time: 2 minutes Mold release temperature: Release of mold clamping pressure after cooling to 130° C.

Cooling temperature: 50° C.

The obtained surface-shaped sheet was observed under an optical microscope. Through this observation, it was confirmed that the cross-sectional area of recesses of the surface-shaped sheet as a percentage relative to the cross-sectional area of protrusions of the mold was 92%, which is a good result. This result demonstrates that excellent surface shaping properties can be obtained even in the case of a sheet-shaped molded product that is relatively thick.

Reference Comparative Example 1

A composition (CE1) was prepared in the same way as in Example 1 with the exception that the methacrylic resin compositions used in Example 1 were changed to 100 parts by mass of the composition (2) obtained in Production Example 2.

It was confirmed that the chemical composition of the obtained pelletized composition (CE1) comprised structural units derived from the monomers MMA, phMI, and chMI in proportions of 81.3 mass %, 7.9 mass %, and 10.8 mass %, respectively.

The weight average molecular weight was 141,000, the Vicat softening temperature was 129° C., and the S/H ratio used as an indicator of stereoregularity was 1.19.

Other evaluation results are shown in Tables 1 and 2.

Reference Comparative Example 2

A composition (CE2) was prepared in the same way as in Example 1 with the exception that the methacrylic resin compositions used in Example 1 were changed to 100 parts by mass of the composition (3) obtained in Production Example 3.

It was confirmed that the chemical composition of the obtained pelletized composition (CE2) comprised structural units derived from the monomers MMA, phMI, and chMI in proportions of 81.3 mass %, 7.9 mass %, and 10.8 mass %, respectively.

The weight average molecular weight was 140,000, the Vicat softening temperature was 128° C., and the S/H ratio used as an indicator of stereoregularity was 1.15.

Other evaluation results are shown in Tables 1 and 2.

Reference Comparative Example 3

A composition (CE3) was prepared in the same way as in Example 3 with the exception that the methacrylic resin compositions used in Example 3 were changed to 100 parts by mass of the composition (4-3) obtained in Production Example 4-3.

It was confirmed that the chemical composition of the obtained pelletized composition (CE3) comprised lactone ring structural units in a proportion of 28.3 mass % and styrene monomer-derived structural units in a proportion of 6.5 mass %.

The weight average molecular weight was 135,000, the Vicat softening temperature was 121° C., and the S/H ratio used as an indicator of stereoregularity was 1.28.

Other evaluation results are shown in Tables 1 and 2.

Reference Comparative Example 4

A methyl methacrylate-maleic anhydride-styrene copolymer (copolymer A) was obtained by a method described in JP S63-1964 B.

The obtained methyl methacrylate-maleic anhydride-styrene copolymer was formed from 74 mass % of methyl methacrylate, 10 mass % of maleic anhydride, and 16 mass % of styrene, and had a weight average molecular weight of 121,000.

A resin composition was prepared in the same way as in Example 1 with the exception that the copolymer A obtained as set forth above was used instead of the methacrylic resin obtained in Production Example 1-1 and 1-2.

The weight average molecular weight was 117,000, the Vicat softening temperature was 122° C., and the S/H ratio used as an indicator of stereoregularity was 1.96.

Comparative Example 5

A composition (9) was prepared in the same way as in Example 1 with the exception that the methacrylic resin compositions used in Example 1 were changed to 55 parts by mass of the composition (2) obtained in Production Example 2 and 45 parts by mass of the polymerized product (5) obtained in Production Example 5. It was confirmed that the chemical composition of the obtained pelletized composition (9) comprised structural units derived from the monomers MMA, phMI, and chMI in proportions of 81.3 mass %, 7.9 mass %, and 10.8 mass %, respectively.

The weight average molecular weight was 160,000, the Vicat softening temperature was 131° C., and the S/H ratio used as an indicator of stereoregularity was 1.56.

Other evaluation results are shown in Tables 1 and 2.

Comparative Example 6

A surface shaping test was performed on a sheet-shaped molded product in the same way as in Example 10 with the exception that the methacrylic resin composition that was used was changed to the composition (CE2) obtained in Reference Comparative Example 2.

However, release from the mold was poor and cracking of the molded product occurred, and thus it was not possible to evaluate surface shaping properties of the molded product.

TABLE 1

| | Used raw materials Resin composition | | | | 2: Molecular weight | 3: Vicat softening temperature | | 5: Proportion of methanol-soluble | 6: Photoelastic coefficient |
|---|---|---|---|---|---|---|---|---|---|
| | Type | Parts by mass | Type | Parts by mass | Mw — | Tvicat ° C. | 4: Stereoregularity S/H | content Mass % | $C_R$ $Pa^{-1}$ |
| Example 1 | Production Example 1-1 | 50 | Production Example 1-2 | 50 | 143,000 | 130 | 1.34 | 1.8 | $0.2 \times 10^{-12}$ |
| Example 2 | Production Example 1-1 | 50 | Production Example 1-4 | 50 | 140,000 | 120 | 1.39 | 2.0 | $0.4 \times 10^{-12}$ |

TABLE 1-continued

| | Used raw materials Resin composition | | | | Composition properties | | | | |
|---|---|---|---|---|---|---|---|---|---|
| | | | | | 2: Molecular weight | 3: Vicat softening temperature | | 5: Proportion of methanol-soluble content | 6: Photoelastic coefficient |
| | Type | Parts by mass | Type | Parts by mass | Mw — | Tvicat °C. | 4: Stereoregularity S/H | Mass % | $C_R$ $Pa^{-1}$ |
| Example 3 | Production Example 1-1 | 50 | Production Example 1-5 | 50 | 137,000 | 138 | 1.29 | 2.5 | $0.4 \times 10^{-12}$ |
| Example 4 | Production Example 1-1 | 70 | Production Example 1-2 | 30 | 168,000 | 133 | 1.37 | 1.7 | $0.3 \times 10^{-12}$ |
| Example 5 | Production Example 1-1 | 30 | Production Example 1-2 | 70 | 122,000 | 127 | 1.31 | 2.1 | $0.3 \times 10^{-12}$ |
| Example 6 | Production Example 4-1 | 50 | Production Example 4-2 | 50 | 148,000 | 124 | 1.33 | 4.2 | $1.5 \times 10^{-12}$ |
| Reference Example 7 | Production Example 1-3 | 100 | | | 131,000 | 129 | 1.24 | 2.2 | $0.2 \times 10^{-12}$ |
| Example 8 | Production Example 2 | 60 | Production Example 5* | 40 | 151,000 | 131 | 1.49 | 3.6 | $0.3 \times 10^{-12}$ |
| Reference Example 9 | Production Example 1-1 | 50 | Production Example 1-6 | 50 | 212,000 | 130 | 1.34 | 1.6 | $0.2 \times 10^{-12}$ |
| Reference Comparative Example 1 | Production Example 2 | 100 | | | 141,000 | 129 | 1.19 | 1.8 | $0.2 \times 10^{-12}$ |
| Reference Comparative Example 2 | Production Example 3 | 100 | | | 140,000 | 128 | 1.15 | 8.5 | $0.2 \times 10^{-12}$ |
| Reference Comparative Example 3 | Production Example 4-3 | 100 | | | 135,000 | 121 | 1.28 | 8.7 | $1.5 \times 10^{-12}$ |
| Reference Comparative Example 4 | Copolymer A* | 100 | | | 117,000 | 122 | 1.96 | 6.5 | $2.5 \times 10^{-12}$ |
| Comparative Example 5 | Production Example 2 | 55 | Production Example 5* | 45 | 160,000 | 131 | 1.56 | 3.0 | $0.3 \times 10^{-12}$ |

*Resin

TABLE 2

| | Used raw materials Resin composition | | | | 7: Surface shaping properties Knurling conditions 1 | | |
|---|---|---|---|---|---|---|---|
| | Type | Parts by mass | Type | Parts by mass | Knurling thickness μm | Shape replicability Rank | Process-ability Rank |
| Example 1 | Production Example 1-1 | 50 | Production Example 1-2 | 50 | 9 | Excellent | Excellent |
| Example 2 | Production Example 1-1 | 50 | Production Example 1-4 | 50 | 10 | Excellent | Excellent |
| Example 3 | Production Example 1-1 | 50 | Production Example 1-5 | 50 | 8 | Good | Excellent |
| Example 4 | Production Example 1-1 | 70 | Production Example 1-2 | 30 | 8 | Excellent | Excellent |
| Example 5 | Production Example 1-1 | 30 | Production Example 1-2 | 70 | 9 | Excellent | Excellent |
| Example 6 | Production Example 4-1 | 50 | Production Example 4-2 | 50 | 7 | Excellent | Excellent |
| Reference Example 7 | Production Example 1-3 | 100 | | | 6 | Good | Excellent |
| Example 8 | Production Example 2 | 60 | Production Example 5* | 40 | 6 | Excellent | Excellent |
| Reference Example 9 | Production Example 1-1 | 50 | Production Example 1-6 | 50 | 6 | Good | Good |
| Reference Comparative Example 1 | Production Example 2 | 100 | | | 6 | Good | Good |
| Reference Comparative Example 2 | Production Example 3 | 100 | | | 6 | Good | Poor |

TABLE 2-continued

| | | | | | | | |
|---|---|---|---|---|---|---|---|
| Reference Comparative Example 3 | Production Example 4-3 | 100 | | | 6 | Good | Poor |
| Reference Comparative Example 4 | Copolymer A* | 100 | | | 6 | Good | Poor |
| Comparative Example 5 | Production Example 2 | 55 | Production Example 5* | 45 | 6 | Excellent | Good |

| | Knurling conditions 2: Speed dependence | | | Knurling conditions 3: Temperature dependence | | | |
|---|---|---|---|---|---|---|---|
| | Knurling thickness μm | Shape replicability Rank | Process-ability Rank | Knurling thickness μm | Shape replicability Rank | Process-ability Rank | Storage stability Rank |
| Example 1 | 7 | Excellent | Excellent | 11 | Excellent | Excellent | Excellent |
| Example 2 | 8 | Excellent | Excellent | 11 | Excellent | Excellent | Excellent |
| Example 3 | 6 | Good | Excellent | 10 | Excellent | Excellent | Excellent |
| Example 4 | 6 | Good | Excellent | 10 | Excellent | Excellent | Excellent |
| Example 5 | 7 | Excellent | Good | 12 | Excellent | Excellent | Excellent |
| Example 6 | 4 | Excellent | Good | 10 | Excellent | Good | Good |
| Reference Example 7 | 3 | Good | Excellent | 7 | Excellent | Good | Good |
| Example 8 | 4 | Excellent | Good | 7 | Excellent | Good | Good |
| Reference Example 9 | 4 | Good | Good | 7 | Good | Good | Good |
| Reference Comparative Example 1 | 3 | Poor | Good | 7 | Good | Good | Good |
| Reference Comparative Example 2 | 3 | Poor | Poor | 7 | Good | Poor | Poor |
| Reference Comparative Example 3 | 3 | Poor | Poor | Evaluation not possible | Evaluation not possible | Poor | Poor |
| Reference Comparative Example 4 | 2 | Poor | Poor | Evaluation not possible | Evaluation not possible | Poor | Poor |
| Comparative Example 5 | 3 | Good | Poor | 7 | Good | Good | Good |

*Resin

It can be clearly seen from Tables 1 and 2 that the films in the examples, which were each formed from a methacrylic resin composition according to the present embodiment, had excellent surface shaping properties by knurling or the like and excellent durability thereof. On the other hand, it can be seen that when the S/H ratio used as an indicator of stereoregularity or the methanol-soluble content is outside of the disclosed range, as in the case of the films in the comparative examples, surface shaping properties and/or durability thereof are poor.

INDUSTRIAL APPLICABILITY

The method for manufacturing a methacrylic resin composition comprising a methacrylic resin composition according to the present embodiment has excellent transparency, and good heat resistance and weather resistance, and the birefringence thereof is controlled to a high degree. Therefore, the method for manufacturing a methacrylic resin composition comprising the methacrylic resin composition according to the present embodiment is suitable for use as an optical material in, for example, polarizing plate protective films, retardation plates (for example, quarter-wave plates and half-wave plates), liquid-crystal optical compensation films (for example, viewing angle control films), display front plates, display base plates, lenses, and the like used in displays such as liquid-crystal displays, plasma displays, organic EL displays, field emission displays, and rear projection televisions. The method for manufacturing a methacrylic resin composition comprising the methacrylic resin composition according to the present embodiment is also suitable for use as an optical material in transparent base plates of solar cells, transparent conductive base plates of touch panels and the like, and may also be used in the fields of optical communication systems, optical switching systems, and optical measurement systems for waveguides, lenses, lens arrays, optical fibers, optical fiber coating materials, LED lenses, lens covers, and so forth.

The invention claimed is:

1. A method for manufacturing a methacrylic resin composition, the method comprising:
   mixing a low molecular weight methacrylic resin having a weight average molecular weight (Mw) of 70,000 to 157,000 and a ratio (S/H) of integrated intensity (S) of a syndiotactic fraction (rr) relative to integrated intensity (H) of a heterotactic fraction (mr), as determined by $^1$H-NMR measurement, is 1.10 to 1.40, and a high molecular weight methacrylic resin having a weight average molecular weight (Mw) of 185,000 to 800,000 and a ratio (S/H) of integrated intensity (S) of a syndiotactic fraction (rr) relative to integrated intensity (H) of a heterotactic fraction (mr), as determined by $^1$H-NMR measurement, is 1.30 to 1.95,
   wherein
   the low molecular weight methacrylic resin and the high molecular weight methacrylic resin each have a structural unit (X) having same cyclic structure-containing main chain and said cyclic structure-containing main chain includes a lactone ring structural unit, the methacrylic resin composition comprises the low molecular weight methacrylic resin and the high molecular weight methacrylic resin, the methacrylic resin composition has a Vicat softening temperature of 120° C. to 160° C., methanol-soluble content is contained in an amount of 5 mass % or less relative to 100 mass %, in total, of the methanol-soluble content and methanol-insoluble content, and a total content of the lactone ring structural units is 5 mass % to 40 mass % relative to 100 mass % of the methacrylic resin composition.

2. The method for manufacturing a methacrylic resin composition according to claim 1, wherein the methacrylic resin composition has a weight average molecular weight (Mw) of 120,000 to 200,000 as measured by gel permeation chromatography as a polymethyl methacrylate equivalent molecular weight.

3. The method for manufacturing a methacrylic resin composition according to claim 1, wherein the methacrylic resin composition has a photoelastic coefficient with an absolute value of $2.0 \times 10^{-12}$ $Pa^{-1}$ or less.

4. The method for manufacturing a methacrylic resin composition according to claim 3, wherein the methacrylic resin composition has a photoelastic coefficient with an absolute value of $1.0 \times 10^{-12}$ $Pa^{-1}$ or less.

* * * * *